(12) United States Patent
Gao

(10) Patent No.: US 11,266,624 B2
(45) Date of Patent: Mar. 8, 2022

(54) CRM1 INHIBITORS REDUCE PRIMARY AND ACQUIRED RESISTANCE OF EGFR INHIBITORS IN LUNG CANCER CELLS

(71) Applicant: Texas Tech University System, Lubbock, TX (US)

(72) Inventor: Weimin Gao, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/374,026

(22) Filed: Apr. 3, 2019

(65) Prior Publication Data

US 2019/0298687 A1 Oct. 3, 2019

Related U.S. Application Data

(60) Provisional application No. 62/652,027, filed on Apr. 3, 2018.

(51) Int. Cl.

| | | |
|---|---|---|
| *A61K 31/366* | (2006.01) | |
| *A61K 31/519* | (2006.01) | |
| *A61K 31/5377* | (2006.01) | |
| *A61K 31/517* | (2006.01) | |
| *A61P 35/00* | (2006.01) | |
| *A61K 31/4439* | (2006.01) | |
| *A61K 31/4245* | (2006.01) | |
| *A61K 31/506* | (2006.01) | |
| *A61K 31/4196* | (2006.01) | |
| *A61K 31/4412* | (2006.01) | |

(52) U.S. Cl.
CPC ........ *A61K 31/366* (2013.01); *A61K 31/4196* (2013.01); *A61K 31/4245* (2013.01); *A61K 31/4412* (2013.01); *A61K 31/4439* (2013.01); *A61K 31/506* (2013.01); *A61K 31/517* (2013.01); *A61K 31/519* (2013.01); *A61K 31/5377* (2013.01); *A61P 35/00* (2018.01)

(58) Field of Classification Search
CPC .............. A61K 31/366; A61K 31/4196; A61K 31/4245; A61K 31/4415; A61K 31/4439; A61K 31/506; A61K 31/517; A61K 31/519; A61K 31/5377; A61P 35/00
See application file for complete search history.

(56) References Cited

U.S. PATENT DOCUMENTS

| | | | | |
|---|---|---|---|---|
| 2008/0038316 A1* | 2/2008 | Wong | .................... | A61K 9/0024 424/426 |
| 2012/0107234 A1* | 5/2012 | Pedersen | ............ | A61K 47/6851 424/1.49 |
| 2013/0203986 A1* | 8/2013 | Yang | .................... | C07D 473/16 544/118 |
| 2015/0175708 A1* | 6/2015 | Aldaz | .................... | C07K 16/30 424/136.1 |
| 2016/0120868 A1* | 5/2016 | Zhang | .................... | A61K 45/06 514/262.1 |
| 2016/0159820 A1* | 6/2016 | Zhou | .................... | C07D 498/04 514/230.5 |
| 2016/0257682 A1* | 9/2016 | Bryan | ................ | A61K 31/5377 |

FOREIGN PATENT DOCUMENTS

WO WO-2015183983 A1 * 12/2015 ............. A61K 31/12

OTHER PUBLICATIONS

Rossi et al., Expert Review of Respiratory Medicine, 2017, Taylor & Francis, vol. 11(3), pp. 171-180 (Year: 2017).*
Mathew et al., Frontiers in Microbiology, 2017, vol. 8, pp. 1-20 (Year: 2017).*
Liu et al., Toxicology & Applied Pharmacology, Sep. 21, 2017, Elsevier, vol. 335, pp. 16-27 (Year: 2017).*
Pao, W., et al., "Acquired resistance of lung adenocarcinomas to gefitinib or erlotinib is associated with a second mutation in the EGFR kinase domain." PLoS Med. (2005), 2:e73.
Pao, W., et al., "KRAS mutations and primary resistance of lung adenocarcinomas to gefitinib or erlotinib." PLoS Med. (2005), 2:e17.
Pathria, G., et al., "Inhibition of CRM1-mediated nucleocytoplasmic transport: triggering human melanoma cell apoptosis by perturbing multiple cellular pathways." J. Invest. Dermatol. (2012), 132:2780-2790.
Peinado, H., et al., "Snail, Zeb and bHLH factors in tumour progression: an alliance against the epithelial phenotype?" Nat. Rev. Cancer. (2007), 7:415-428.
Posadas, E.M., et al., "A phase II and pharmacodynamic study of gefitinib in patients with refractory or recurrent epithelial ovarian cancer." Cancer (2007), 109:1323-1330.
Rho, J.K., et al., "Epithelial to mesenchymal transition derived from repeated exposure to gefitinib determines the sensitivity to EGFR inhibitors in A549, a non-small cell lung cancer cell line." Lung Cancer (2009), 63:219-226.
Segovia-Mendoza, M., et al., "Efficacy and mechanism of action of the tyrosine kinase inhibitors gefitinib, lapatinib and neratinib in the treatment of HER2-positive breast cancer: preclinical and clinical evidence." Am. J. Cancer Res. (2015), 5:2531-2561.
Shao, C., et al., "p53-Dependent anticancer effects of leptomycin B on lung adenocarcinoma." Cancer Chemother. Pharmacol. (2011), 67:1369-1380.

(Continued)

*Primary Examiner* — Sarah Pihonak
(74) *Attorney, Agent, or Firm* — Edwin S. Flores; Daniel J. Chalker; Chalker Flores, LLP

(57) ABSTRACT

The present invention includes a method and compositions for preventing primary or acquired resistance of epidermal growth factor receptors (EGFR) inhibitors in a cancer with deregulated EGFR comprising: identifying a subject suspected of needing treatment for primary or acquired resistance to epidermal growth factor receptor (EGFR) inhibitors of the cancer with deregulated EGFR; and providing the subject with a therapeutically effective amount of a chromosome region maintenance 1 (CRM1) inhibitor and an inhibitor of EGFR in an amount sufficient to reduce or eliminate the cancer.

5 Claims, 11 Drawing Sheets
Specification includes a Sequence Listing.

(56) References Cited

OTHER PUBLICATIONS

Shen, L., et al., "The synergistic effect of EGFR tyrosine kinase inhibitor gefitinib in combination with aromatase inhibitor anastrozole in non-small cell lung cancer cell lines." Lung Cancer (2012), 78:193-200.

Sierra, J.R., et al., "Molecular mechanisms of acquired resistance to tyrosine kinase targeted therapy." Mol. Cancer. (2010), 9:75.

Sos, M.L., et al., "Chemogenomic profiling provides insights into the limited activity of irreversible EGFR Inhibitors in tumor cells expressing the T790M EGFR resistance mutation." Cancer Res. (2010), 70:868-874.

Sun, K.K., et al., "Transducer of erbB2. 1 is a potential cellular target of gefitinib in lung cancer therapy." Oncol. Lett. (2013), 5:373-377.

Tartarone, A., et al., Mechanisms of resistance to EGFR tyrosine kinase inhibitors gefitinib/erlotinib and to ALK inhibitor crizotinib. Lung Cancer (2013), 81:328-336.

Turner, J.G., et al., "Inhibition of CRM1-dependent nuclear export sensitizes malignant cells to cytotoxic and targeted agents, Seminars in cancer biology." Semin. Cancer Biol. (2014), 27:62-73.

Wang, S., et al., "Antitumor effects of a novel chromosome region maintenance 1 (CRM1) inhibitor on non-small cell lung cancer cells in vitro and in mouse tumor xenografts." PLoS One (2014), 9:e89848.

Wang, Y., et al., "miR-138-1* regulates aflatoxin B1-induced malignant transformation of BEAS-2B cells by targeting PDK1." Arch. Toxicol. (2016), 90:1239-1249.

Yamamoto, C., et al., "Loss of PTEN expression by blocking nuclear translocation of EGR1 in gefitinib-resistant lung cancer cells harboring epidermal growth factor receptor-activating mutations." Cancer Res. (2010), 70:8715-8725.

Yang, J., et al., "Epithelial-mesenchymal transition: at the crossroads of development and tumor metastasis." Dev. Cell (2008), 14:818-829.

Zhao, R., et al., "AT-101 enhances gefitinib sensitivity in non-small cell lung cancer with EGFR T790M mutations." BMC cancer (2016), 16:491.

Zhou, X., et al., "Gefitinib inhibits the proliferation of pancreatic cancer cells via cell cycle arrest." Anat. Rec. (2009), 292:1122-1127.

Zhao, Z.Q., et al., "Gefitinib induces lung cancer cell autophagy and apoptosis via blockade of the PI3K/AKT/mTOR pathway." Oncol Lett. (2016), 12:63-68.

Zhu, Y., et al., "Resveratrol overcomes gefitinib resistance by increasing the intracellular gefitinib concentration and triggering apoptosis, autophagy and senescence in PC9/G NSCLC cells." Sci Rep. (2015), 5:17730.

Adachi, M., et al., "Nuclear Export of Map Kinase (ERK) Involves a Map Kinase Kinase (Mek-Dependent) Active Transport Mechanism." J. Cell Biol. (2000), 148:849-856.

Alt, J.R., et al., "p21Cip1 promotes cyclin D1 nuclear accumulation via direct inhibition of nuclear export." J. Biol. Chem. (2002), 277:8517-8523.

Azmi, A.S., et al., "Targeting the nuclear export protein XPO1/CRM1 reverses epithelial to mesenchymal transition." Sci. Rep. (2015), 5:16077.

Cagnol, S., et al., "ERK and cell death: Mechanisms of ERK-induced cell death—apoptosis, autophagy and senescence." FEBS J. (2010), 277:2-21.

Chao, T.-T., et al., "Afatinib induces apoptosis in NSCLC without EGFR mutation through Elk-1-mediated suppression of CIP2A." Oncotarget (2015), 6:2164.

Chen, J., et al., "Atorvastatin overcomes gefitinib resistance in KRAS mutant human non-small cell lung carcinoma cells." Cell Death Dis. (2013), 4:e814.

Chiu, H.-C., et al., "Suppression of Stat3 activity sensitizes gefitinib-resistant non small cell lung cancer cells." Biochem. Pharmacol. (2011), 81:1263-1270.

Cho, S.H., et al., "CD44 enhances the epithelial-mesenchymal transition in association with colon cancer invasion." Int. J. Oncol. (2012), 41:211-218.

Conde, E., et al., "Molecular context of the EGFR mutations: evidence for the activation of mTOR/S6K signaling." Clin. Cancer Res. (2006), 12:710-717.

Cortot, A.B., et al., "Molecular mechanisms of resistance in epidermal growth factor receptor-mutant lung adenocarcinomas." Eur. Respir. Rev. (2014), 23:356-366.

Cromie, M.M., et al., "Epigallocatechin-3-gallate enhances the therapeutic effects of leptomycin B on human lung cancer a549 cells." Oxid. Med. Cell Longev. (2015), Article ID 217304.

Dragnev, K., et al., "Lung cancer chemoprevention: difficulties, promise and potential agents?" Expert Opin. Investig. Drugs. (2013), 22:35-47.

Du, J., et al., "MicroRNA-221 targets PTEN to reduce the sensitivity of cervical cancer cells to gefitinib through the PI3K/Akt signaling pathway." Tumor Biol. (2016), 37:3939-3947.

Engelman, J.A., et al., "MET amplification leads to gefitinib resistance in lung cancer by activating ERBB3 signaling." Science (2007), 316:1039-1043.

Gao, W., et al., "Overexpression of CRM1: a characteristic feature in a transformed phenotype of lung carcinogenesis and a molecular target for lung cancer adjuvant therapy." J. Thorac. Oncol. (2015), 10:815-825.

Ghosh, G., et al., "Properties of resistant cells generated from lung cancer cell lines treated with EGFR inhibitors." BMC cancer (2012), 12:95.

Goncalves, A., et al., "A phase II trial to evaluate gefitinib as second-or third-line treatment in patients with recurring locoregionally advanced or metastatic cervical cancer." Gynecol Oncol. (2008), 108:42-46.

Gridelli, C., et al., "Gefitinib as first-line treatment for patients with advanced non-small-cell lung cancer with activating epidermal growth factor receptor mutation: Review of the evidence." Lung Cancer (2011), 71:249-257.

Home, M., "Should EGFR Tyrosine Kinase Inhibitors Be Used in Non-Small Cell Lung Cancer in the Absence of EGFR Mutations?" Clinical Advances in Hematology & Oncology (2016), 14:41-45.

Huang, M.-H., et al., "MEK inhibitors reverse resistance in epidermal growth factor receptor mutation lung cancer cells with acquired resistance to gefitinib." Mol. Oncol. (2013), 7:112-120.

Huang, Y.-C.T., "Outdoor air pollution: a global perspective." J. Occup. Environ. Med. (2014), 56:S3-S7.

Jin, H.O., et al., "Combined effects of EGFR tyrosine kinase inhibitors and vATPase inhibitors in NSCLC cells." Toxicol Appl Pharmacol. (2015), 287:17-25.

Kancha, R.K., et al., "Imatinib and leptomycin B are effective in overcoming imatinib-resistance due to Bcr-Abl amplification and clonal evolution but not due to Bcr-Abl kinase domain mutation." Haematologica (2008), 93:1718-1722.

Kazandjian, D., et al., "FDA Approval of Gefitinib for the Treatment of Patients with Metastatic EGFR Mutation—Positive Non-Small Cell Lung Cancer." Clin. Cancer Res. (2016), 22:1307-1312.

Kim, J., et al., "XPO1-dependent nuclear export is a druggable vulnerability in KRAS-mutant lung cancer." Nature (2016), 538:114-117.

Koehler, J., et al., "Afatinib, erlotinib and gefitinib in the first-line therapy of EGFR mutation-positive lung adenocarcinoma: a review." Onkologie. (2013), 36:510-518.

Koizumi, F., et al., "Establishment of a human non small cell lung cancer cell line resistant to gefitinib." Int.J. Cancer. (2005), 116:36-44.

Kwak, E.L., et al., "Irreversible inhibitors of the EGF receptor may circumvent acquired resistance to gefitinib." Proc. Natl. Acad. Sci. U S A. (2005), 102:7665-7670.

Lee, C.K., et al., "Impact of EGFR inhibitor in non-small cell lung cancer on progression-free and overall survival: a meta-analysis." J. Natl. Cancer Inst. (2013), 105:595-605.

Li, N., et al., "Relationship between epidermal growth factor receptor (EGFR) mutation and serum cyclooxygenase-2 Level, and

(56) References Cited

OTHER PUBLICATIONS the synergistic effect of celecoxib and gefitinib on EGFR expression in non-small cell lung cancer cells." Int. J. Clin. Exp. Pathol. (2015), 8:9010.

Li, S., et al., "Synergistic interaction between MEK inhibitor and gefitinib in EGFR TKI resistant human lung cancer cells." Oncol. Lett. (2015), 10:2652-2656.

Lo, H.W., et al., "Nuclear cytoplasmic transport of EGFR involves receptor endocytosis, importin β1 and CRM1." J. Cell Biochem. (2006), 98:1570-1583.

Lu, C., et al., "Chemotherapeutic sensitization of leptomycin B resistant lung cancer cells by pretreatment with doxorubicin." PLoS One (2012), 7:e32895.

Lu, C., et al., "Nuclear Export as a Novel Therapeutic Target: The CRM1 Connection." Curr. Cancer Drug Targets (2015), 15:575-592.

Lv, T., et al., "Twist1-mediated 4E-BP1 regulation through mTOR in non-small cell lung cancer." Oncotarget (2015), 6:33006-33018.

Mani, S.A., et al., "The epithelial-mesenchymal transition generates cells with properties of stem cells." Cell (2008), 133:704-715.

Marquez-Medina, D., et al., "Eventual role of EGFR-tyrosine kinase inhibitors in early-stage non-small-cell lung cancer." Future Oncol. (2016), (2016), 12:815-825.

Meloche, S., et al., "The ERK1/2 mitogen-activated protein kinase pathway as a master regulator of the G1-to S-phase transition." Oncogene (2007), 26:3227-3239.

Mukohara, T., et al., "Differential effects of gefitinib and cetuximab on non-small-cell lung cancers bearing epidermal growth factor receptor mutations." J. Natl. Cancer Inst. (2005), 97:1185-1194.

Mutka, S.C., et al., "Identification of nuclear export inhibitors with potent anticancer activity in vivo." Cancer Res. (2009), 69:510-517.

Nakaya, Y., et al., "EMT in developmental morphogenesis." Cancer Lett. (2013), 341:9-15.

Newlands, E., et al., "Phase I trial of elactocin." Br. J. Cancer. (1996), 74:648-649.

Nguyen, K.-S.H., et al., "Acquired resistance to epidermal growth factor receptor tyrosine kinase inhibitors in non-small-cell lung cancers dependent on the epidermal growth factor receptor pathway." Clin. lung Cancer (2009), 10:281-289.

Ohta, T., et al., "Gefitinib (ZD1839) increases the efficacy of cisplatin in ovarian cancer cells." Cancer Biol. Ther. (2012), 13:408-416.

Okamoto, K., et al., "Role of survivin in EGFR inhibitor-induced apoptosis in non-small cell lung cancers positive for EGFR mutations." Cancer Res. (2010), 70:10402-10410.

Okamoto, K., et al., "Overcoming erlotinib resistance in EGFR mutation-positive non-small cell lung cancer cells by targeting survivin." Mol. Cancer Ther. (2012), 11:204-213.

\* cited by examiner

CRM1 INHIBITORS REDUCE PRIMARY AND ACQUIRED RESISTANCE OF EGFR INHIBITORS IN LUNG CANCER CELLS

CROSS-REFERENCE TO RELATED APPLICATIONS

This application claims priority to U.S. Provisional Application Ser. No. 62/652,027, filed Apr. 3, 2018, the entire contents of which are incorporated herein by reference.

STATEMENT OF FEDERALLY FUNDED RESEARCH

This invention was made with government support under R15ES026789 awarded by National Institutes of Health/National Institute of Environmental Health Sciences. The government has certain rights in the invention.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Apr. 2, 2019, is named TECH1179_SeqList.txt and is 7, kilobytes in size.

TECHNICAL FIELD OF THE INVENTION

The present invention relates in general to the field of inhibitors of primary or acquired resistance of epidermal growth factor receptor (EGFR) inhibitors in lung and other cancers.

BACKGROUND OF THE INVENTION

Without limiting the scope of the invention, its background is described in connection with treatments for, e.g., lung cancer.

Lung cancer is a leading cause of cancer-related deaths around the world with about 1.3 million deaths per year (Huang, 2014). Histologically, lung cancer can be classified into small-cell lung cancer and non-small cell lung cancer (NSCLC) with 80-85% being NSCLC (Dragnev et al., 2013), most of which are diagnosed at an advanced stage of the disease and have a poor long-term survival from curative surgery or radiation therapy (Marquez-Medina and Popat, 2016). In particular, mutated and overactive epidermal growth factor receptor (EGFR) in NSCLC has emerged as a unique subset of lung adenocarcinoma (Koehler and Schuler, 2013), and targeting the dysregulated EGFR with tyrosine kinase inhibitors (TKIs) have been developed to treat locally advanced or metastatic NSCLC (Lee et al., 2013).

One of such EGFR TKIs is gefitinib (commercial name Iressa; AstraZeneca UK limited) which has been recently approved by FDA as a first-line treatment for metastatic EGFR mutation-positive NSCLC patients (Kazandjian et al., 2016), though recent studies revealed that some NSCLC patients without EGFR mutation(s) also respond to TKIs including gefitinib (the first generation) and afatinib (the second generation) (Home, 2016; Gridelli et al., 2011; Chao et al., 2015). Although EGFR TKI therapies have significantly improved the survival of NSCLC patients, acquired drug resistance eventually emerges and significantly limits the therapeutic potency of EGFR TKI treatments (Koehler and Schuler, 2013). Secondary somatic T790M mutation in EGFR exon 20 and amplification of MET were frequently identified as the underling mechanisms for EGFR TKI acquired resistance, which have been reported in up to 70% of cases among patients (Pao et al., 2005a; Engelman et al., 2007; Sos et al., 2010). Other resistance mechanisms may exist and need to be further explored. For instance, it has been suggested that epithelial-mesenchymal transition (EMT) may contribute to the acquired resistance to gefitinib (Rho et al., 2009), by which cancer cells demonstrate morphological changes from the epithelial polarized phenotype to the mesenchymal fibroblastoid phenotype, and thereby enhance their mobility and invasiveness (Nakaya and Sheng, 2013).

However, while gefitinib has demonstrated dramatic clinical efficacy in non-small cell lung cancer (NSCLC) patients, its therapeutic efficacy is ultimately limited by the development of acquired drug resistance.

Thus, a need remains for effective treatments for every stage of lung cancer, including lung cancers that become refractory to initial therapies.

SUMMARY OF THE INVENTION

In one embodiment, the present invention includes a method for preventing primary or acquired resistance of epidermal growth factor receptors (EGFR) inhibitors in a cancer with deregulated EGFR comprising: identifying a subject suspected of needing treatment for primary or acquired resistance to epidermal growth factor receptor (EGFR) inhibitors of the cancer with deregulated EGFR; and providing the subject with a therapeutically effective amount of a chromosome region maintenance 1 (CRM1) inhibitor and an inhibitor of EGFR in an amount sufficient to reduce or eliminate the cancer. In one aspect, the CRM1 inhibitor is selected from Leptomycin B (LMB), 1-((6-chloro-5-(trifluoromethyl)pyridin-2-yl)amino)-3-((3,3-dimethylbutoxy)methyl)-4-methyl-1H-pyrrole-2,5-dione (CBS-9106), (Z)-2-(2-(3-(3,5-bis(trifluoromethyl)phenyl)-1H-1,2,4-triazol-1-yl)vinyl)-1,3,4-oxadiazole (KPT251), Piperlongumine, Verdinexor (KPT-335), Eltanexor (KPT-8602), KPT-276, KPT-185, or Selinexor (KPT-330). In another aspect, the cancers are selected from breast, lung, colon, or pancreatic cancer. In another aspect, the cancer is a lung cancer selected from non-small cell lung cancer, a lung adenocarcinoma, or a bronchioloalveolar carcinoma. In another aspect, the EGFR inhibitor is selected from gefitinib, afatinib, brigatinib, icotinib, cetuximab, lapatinib, erlotinib, osimertinib, or olmutinib. In another aspect, the deregulated EGFR is at least one of a mutated EGFR, an over-expressed EGFR, or overactive EGFR. In another aspect, the deregulated EGFR is at least one of a mutated Y992, Y1045, Y1068, Y1148, or Y1173 EGFR mutant. In another aspect, the combination of the CRM1 inhibitor and the EGRF inhibitor is synergistic.

In another embodiment, the present invention includes a method for preventing primary or acquired resistance of epidermal growth factor receptors (EGFR) inhibitors in a lung cancer comprising: identifying a subject suspected of needing treatment for primary or acquired resistance of epidermal growth factor receptor (EGFR) inhibitors in lung cancer; and providing the subject with a synergistic amount of a chromosome region maintenance 1 (CRM1) inhibitor and an EGFR inhibitor sufficient to reduce or eliminate the cancer. In one aspect, the CRM1 inhibitor is selected from Leptomycin B (LMB), 1-((6-chloro-5-(trifluoromethyl)pyridin-2-yl)amino)-3-((3,3-dimethylbutoxy)methyl)-4-methyl- 1H-pyrrole-2,5-dione (CBS-9106), (Z)-2-(2-(3-(3,5-bis(trifluoromethyl)phenyl)-1H-1,2,4-triazol-1-yl)vinyl)-1,3,4-oxadiazole (KPT251), Piperlongumine, Verdinexor (KPT-335), Eltanexor (KPT-8602), KPT-276, KPT-185, or Selinexor (KPT-330). In another aspect, the cancer is a lung cancer selected from non-small cell lung cancer, a lung adenocarcinoma, or a bronchioloalveolar carcinoma. In another aspect, the EGFR inhibitor is selected from gefitinib, afatinib, brigatinib, icotinib, cetuximab, lapatinib, erlotinib, osimertinib, or olmutinib. In another aspect, the deregulated EGFR is at least one of a mutated EGFR, an over-expressed EGFR, or overactive EGFR. In another aspect, the deregulated EGFR is at least one of a mutated Y992, Y1045, Y1068, Y1148 and Y1173 EGFR.

In yet another embodiment, the present invention includes a composition comprising an amount of a CRM1 inhibitor and an EGRF inhibitor that is synergistic when compared to the additive effect of the CRM1 inhibitor and the EGRF inhibitor when used alone. In one aspect, the CRM1 inhibitor is selected from Leptomycin B (LMB), 1-((6-chloro-5-(trifluoromethyl)pyridin-2-yl)amino)-3-((3,3-dimethylbutoxy)methyl)-4-methyl-1H-pyrrole-2,5-dione (CBS-9106), (Z)-2-(2-(3-(3,5-bis(trifluoromethyl)phenyl)-1H-1,2,4-triazol-1-yl)vinyl)-1,3,4-oxadiazole (KPT251), Piperlongumine, Verdinexor (KPT-335), Eltanexor (KPT-8602), KPT-276, KPT-185, or Selinexor (KPT-330). In another aspect, the cancer is a lung cancer selected from non-small cell lung cancer, a lung adenocarcinoma, or a bronchioloalveolar carcinoma. In another aspect, the EGFR inhibitor is selected from gefitinib, afatinib, brigatinib, icotinib, cetuximab, lapatinib, erlotinib, osimertinib, or olmutinib. In another aspect, the composition is adapted for oral, intranasal, pulmonary, intraperitoneal, intravenous, vaginal, rectal, intramuscular, aerosol, nasal spray, transdermal, or colonic administration. In another aspect, the composition further comprises one or more pharmaceutically acceptable carriers. In another aspect, the composition is adapted for sustained release.

In another embodiment, the present invention includes a method for treating acquired resistance of epidermal growth factor receptors (EGFR) inhibitors in a lung cancer comprising: identifying a subject suspected of needing treatment for acquired resistance of epidermal growth factor receptor (EGFR) inhibitors in lung cancer; and providing the subject with a synergistic amount of a chromosome region maintenance 1 (CRM1) inhibitor and an EGFR inhibitor sufficient to reduce or eliminate the cancer. In one aspect, the CRM1 inhibitor is selected from Leptomycin B (LMB), 1-((6-chloro-5-(trifluoromethyl)pyridin-2-yl)amino)-3-((3,3-dimethylbutoxy)methyl)-4-methyl-1H-pyrrole-2,5-dione (CBS-9106), (Z)-2-(2-(3-(3,5-bis(trifluoromethyl)phenyl)-1H-1,2,4-triazol-1-yl)vinyl)-1,3,4-oxadiazole (KPT251), Piperlongumine, Verdinexor (KPT-335), Eltanexor (KPT-8602), KPT-276, KPT-185, or Selinexor (KPT-330). In another aspect, the cancer is a lung cancer with acquired resistance to EGFR inhibitors selected from non-small cell lung cancer, a lung adenocarcinoma, or a bronchioloalveolar carcinoma. In another aspect, the EGFR inhibitor is selected from gefitinib, afatinib, brigatinib, icotinib, cetuximab, lapatinib, erlotinib, osimertinib, or olmutinib. In another aspect, the deregulated EGFR is at least one of a mutated EGFR, an over-expressed EGFR, or overactive EGFR. In another aspect, the deregulated EGFR is at least one of a mutated Y992, Y1045, Y1068, Y1148 and Y1173 EGFR.

BRIEF DESCRIPTION OF THE DRAWINGS

For a more complete understanding of the features and advantages of the present invention, reference is now made to the detailed description of the invention along with the accompanying figures and in which:

(FIG. 1C) Representative histograms of cell cycle analyses in gefitinib and LMB-treated A549 for 48 hrs were shown. Control, LMB, Gefitinib12, Gefitinib12+LMB, Gefitinib24, and Gefitinib24+LMB were harvested and labeled with Guava Cell Cycle Reagent (Millipore) and analyzed by flow cytometry (pre-G1, G0/G1, S, and G2/M). The y-axis shows the number of cells counted and the x-axis shows an increasing amount of Guava Cell Cycle Reagent incorporation/cell (left to right). Experiments performed in triplicate yielded similar results. LMB: 0.5 nM LMB, Gefitinib12: 12 µM gefitinib, and Gefitinib24: 24 µM gefitinib.

FIG. 2A shows the effects of gefitinib+LMB treatment on the protein expression of EGFR, p-EGFR(Tyr1068), Akt, p-Akt (Ser473), Erk1/2, p-Erk1/2(Thr202/Tyr204), survivin, and p21. After 48 hrs treatment, cells were harvested for Western blot analysis to determine protein levels. Blots were also probed for α-tubulin to confirm equal protein loading.

(FIG. 4A) Morphological images (magnifications ×200) of A549, A549GR, and A549GLR. (FIG. 4B) Microscopic images (magnifications ×100) of colonies of A549, A549GR, and A549GLR in soft agar. (FIG. 4C) Colony number and (FIG. 4D) size of A549, A549GR, and A549GLR in anchorage-independent growth assay. Data are represented as mean±SD, n=12. (FIG. 4E) Microscopic images (×40) of wound healing closures of A549, A549GR, and A549GLR obtained at 0 to 48 hrs after pipette scratching. (FIG. 4F) The migrating distances of A549, A549GR, and A549GLR over 48 hrs in the wound healing assay. Data are represented as mean±SD, n=18. The wound closure rates of A549GR and A549GLR are significantly larger than A549 at 48 hrs (p<0.05). (FIG. 4G) The number of cells counted on the bottom side of cell culture inserts in the transwell invasion assay. Data are represented as mean±SD, n=10. Mean values within the same column containing different superscript letters indicates a significant difference among the treatment groups analyzed by a one-way ANOVA followed by a Fisher's LSD test (p<0.05). Values bearing the letter "a" indicate no significant differences compared with A549, those labeled "b" denote a significant difference when compared with the A549, and "c" denotes a significant difference when A549GLR is compared with A549GR.

(FIG. 5A) Protein expressions of EGFR, p-EGFR(Tyr1068), Akt, p-Akt(Ser473), Erk1/2, p-Erk1/2(Thr202/Tyr204), p-STAT3 (S727), survivin, E-cadherin, vimentin, Twist1, MET, and HER2. Blots were also probed for α-tubulin to confirm equal protein loading. (FIG. 5F) qRT-PCR analysis of EGFR, STAT3, E-cadherin, N-cadherin, vimentin, Twist1, Snail1, CD24, CD44, CD133, MET, and HER2 in A549, A549GR, and A549GLR. Data are represented as mean±SD, n=3. Mean values within the same column containing different superscript letters indicate significant differences among the treatment groups (p<0.05). Values bearing the letter "a" indicate no significant differences compared with A549, those labeled "b" denote a significant difference when compared with A549, and "c" denotes a significant difference when A549 GLR is compared with A549GR.

DETAILED DESCRIPTION OF THE INVENTION

Figure 1A:
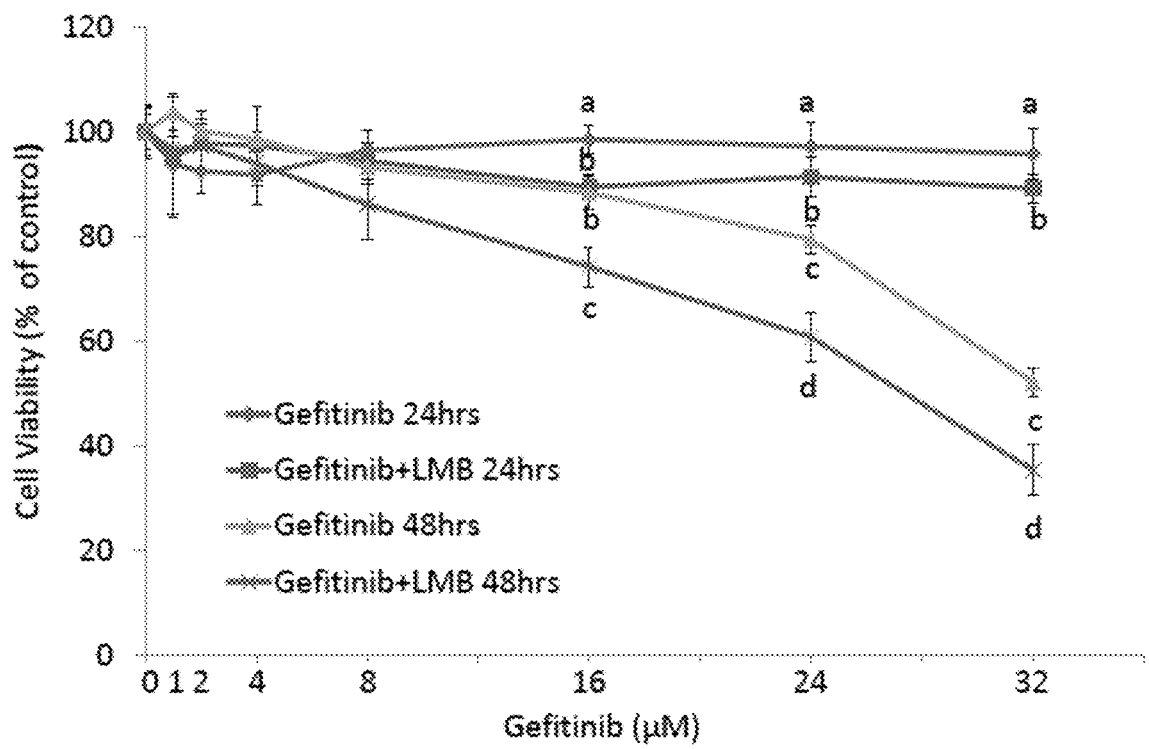
FIGS. 1A to 1C show the cytotoxic effects of gefitinib and/or LMB on (FIG. 1A) A549 and (FIG. 1B) H460 and (FIG. 1C) flow cytometry analyses of cell cycle in A549 after gefitinib and/or LMB treatment. Cytotoxic effects of gefitinib alone and gefitinib+LMB on the cell viability of A549 (FIG. 1A) and H460 (FIG. 1B) were determined by the MTT assays. Data are expressed as the percentage by comparing to vehicle controls for gefitinib treatments or LMB (0.5 nM) for gefitinib+LMB treatments. Values are represented as mean±SD, n=6. Mean values at the same concentration containing different letters indicate a significant difference among the treatment groups analyzed by a one-way ANOVA followed by a Fisher's LSD test (p<0.05).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Abbreviations: CRM1, Chromosome region maintenance 1; EGFR, epidermal growth factor receptor; EMT, epithelial-mesenchymal transition; LMB, leptomycin B; MTT, 3-(4,5-dimetrylthiazol)-2,5-diphenyltetrazolium bromide; NSCLC, non-small cell lung cancer; TKIs, tyrosine kinase inhibitors; T790M, a substitution mutation of threonine with methionine at position 790 of EGFR exon 20.

The present invention demonstrates the utility of chromosome region maintenance 1 (CRM1) inhibitors, such as Leptomycin B (LMB), in combination with gefitinib to overcome primary and acquired gefitinib resistance in NSCLC cells. The combinative effects of gefitinib and LMB were evaluated by MTT and its underlining mechanism was assessed by flow cytometry and Western blot. LMB displayed a synergistic effect on gefitinib-induced cytotoxicity in A549 ($IC_{50}$: 25.0±2.1 µM of gefitinib+LMB vs. 32.0±2.5 µM of gefitinib alone, p<0.05). Gefitinib+LMB caused a significantly different cell cycle distribution and signaling pathways involving in EGFR/survivin/p21 compared with gefitinib. A549 cells then were treated with progressively increasing concentrations of gefitinib (A549GR) or in combination with LMB (A549GLR) over 10 months to generate gefitinib resistance. IC50 of gefitinib in A549GLR (37.0±2.8 µM) was significantly lower than that in A549GR (53.0±3.0 µM, p<0.05), which indicates that LMB could reverse gefitinib-induced resistance in A549. Further mechanism investigation revealed that the expression patterns of EGFR pathway and epithelial-mesenchymal transition (EMT) markers in A549, A549GR, and A549GLR were significantly different. In conclusion, LMB at a very low concentration combined with gefitinib showed synergistic therapeutic effects and ameliorated the development of gefitinib-induced resistance in lung cancer cells.

Chromosome region maintenance 1 (CRM1), also known as exportin 1 (XPO1), is a nuclear export receptor responsible for transporting a variety of cancer related proteins from nucleus to cytoplasm including p53, p21, p27, pRB, FOXO, and EGFR (Lo et al., 2006; Lu et al., 2012; Lu et al., 2015). Previous studies by the present inventors have demonstrated that CRM1 is overexpressed in lung cancer and CRM1 inhibitor, leptomycin B (LMB) could serve as an effective adjuvant regimen for lung cancer treatment (Gao et al., 2015; Lu et al., 2015). A recent study further revealed that KRAS-mutant NSCLC is vulnerable to chemical inhibition of CRM1 (XPO1)-dependent nuclear export (Kim et al., 2016). LMB, as the first generation of pharmaceutical CRM1 inhibitor isolated from *Streptomyces* spp., has shown highly inhibitory efficiency in various cancer cell lines including NSCLC cells (IC50 ranging from 0.1 to 10 nM) (Mutka et al., 2009) and more importantly, LMB demonstrated a great potential to reduce drug resistance in various cancer cells induced by different anticancer therapeutic agents (Lu et al., 2015). In addition, short-term LMB treatment (24-72 hrs) could reverse EMT in snail-transduced primary human mammary epithelial cells (HEMCs) by targeting CRM1 (Azmi et al., 2015). The present inventors recognized that the phase I trial of LMB as a single therapeutic agent was unsuccessful due to its gastrointestinal toxicities like malaise and anorexia (Newlands et al., 1996), these side effects may significantly diminish at lower doses when used as a combinative agent (Gao et al., 2015; Lu et al., 2015). Therefore, the clinical application of LMB as an adjuvant therapy also deserves a thorough re-evaluation and LMB is still used as the paradigm for a novel class of anticancer drugs based on CRM1 inhibition (Gao et al., 2015). Moreover, a series of semi-synthetic LMB derivatives (not commercial available) have been developed, which maintain high potency of LMB and show much better tolerability in vivo than LMB (Mutka et al., 2009).

While combination chemotherapy using EGFR TKIs and drugs with different anticancer mechanisms has demonstrated to be an effective strategies to overcome EGFR TKI resistance or EMT (Huang et al., 2013; Tartarone et al., 2013; Zhu et al., 2015; Zhao et al., 2016a), there are still no reports on the effective combined treatments using CRM1 inhibitors and EGFR TKIs for NSCLC therapy. Moreover, there are no studies investigating the long-term effect of combinative agents on reducing the development of acquired resistance of gefitinib in NSCLC. Also, the effects of inhibiting EMT on the development of EGFR TKI acquired resistance in NSCLC remain unclear.

The present invention is directed to the combined treatment of gefitinib and LMB, which showed a synergistic cytotoxic effect on NSCLC cell lines A549 and H460. The mechanism of this surprising synergism of gefitinib and LMB in A549 was further investigated by flow cytometry and Western blot analyses. A549 co-treated with gefitinib and LMB exhibited significantly different profiles of survival signaling and cell cycle arrest from A549 treated by gefitinib alone. More importantly, the effects of LMB on reducing acquired gefitinib resistance in A549 were testified in A549 generated by co-treatment of gefitinib and LMB for 10 months, which remained a much higher gefitinib-sensitivity compared to gefitinib-resistant A549. Finally, Western blot, quantitative real time PCR (qRT-PCR), and series of phenotype assays revealed that the two resistant A549 cells had significantly different expressions of EGFR pathways and EMT biomarkers as well as malignant transformation activities compared to parental A549 cells.

Formulations. The synergistic composition that includes an EGFR inhibitor and the CRM1 inhibitor of the present invention can be formulated with one or more pharmacological carriers for delivery through one or more routes of drug administration, e.g., intravenous (IV), oral, intranasal, pulmonary, intraperitoneal (IP), vaginal, rectal, intramuscular (IM), aerosol, nasal spray, ocular, transdermal, colonic, and the like.

For intravenous injection, the present invention may be formulated into a generally water soluble versions of the compounds of the present invention are formulated in, or if provided lyophilized, mixed with, or being capable of being mixed with, a physiologically acceptable fluid vehicle, such as 5% dextrose, physiologically buffered saline, 0.9% saline, Hanks' solution, or Ringer's solution. The intravenous formulations of the present invention may include the EGFR inhibitor or antagonist and the CRM1 inhibitor or antagonist in a formulation that may include, e.g., carriers, excipients or stabilizers including, without limitation, calcium, citrate, acetate, calcium chloride, carbonate, and other salts. Intravenous formulations can also include substances that increase the viscosity of the suspension, such as sodium carboxymethyl cellulose, sorbitol, or dextran. Optionally, the intravenous formulations can also contain suitable stabilizers or agents that increase the solubility of the compounds to allow for the preparation of highly concentrated solutions.

The pharmaceutical compositions that include the EGFR inhibitor or antagonist and the CRM1 inhibitor or antagonist may further comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), solubilizing agents or ions such as Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof.

The EGFR inhibitors and CRM1 inhibitors may be formulated into pharmaceutical compositions that permit injectable, long-term, deposition. For example, an injectable depot may be made by forming microencapsulated matrices of the EGFR inhibitors and CRM1 inhibitors in biodegradable and/or biocompatible polymers such as polylactide-polyglycolide. Depending on the ratio of EGFR inhibitors and CRM1 inhibitors to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

These pharmacological carriers can be in a variety of forms. These include, for example, solid, semi-solid and liquid dosage forms, such as tablets, pills, powders, liquid solutions or suspensions, liposomes, injectable and infusible solutions. These agents can also be incorporated into various cosmetic and toiletry formulations, either for therapeutic usage, or to mitigate irritation (or sensitization accompanying these formulations (See Flick E. W. COSMETIC AND TOILETRY FORMULATIONS, 2nd Ed., Noyes Publications, 1989). The preferred form depends on the intended mode of administration and therapeutic application.

While it is possible to administer the active ingredient alone, it is preferable to present it as part of a pharmaceutical formulation. These formulations comprise the pharmacological agent in a therapeutically or pharmaceutically effective dose together with one or more pharmaceutically or therapeutically acceptable carriers and optionally other therapeutic ingredients. Various considerations are described, e.g., in Gilman et al. (eds) (1990) GOODMAN AND GILMAN'S: THE PHARMACOLOGICAL BASES OF THERAPEUTICS, 8th Ed., Pergamon Press; NOVEL DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. See, also, BIOREVERSIBLE CARRIERS IN DRUG DESIGN, THEORY AND APPLICATION, Roche (ed.), Pergamon Press, (1987).

Aerosol Formulations. For delivery to the nasal or bronchial membranes, typically an aerosol formulation will be employed. The term "aerosol" includes any gas-borne suspended phase of the pharmacological agent, which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the pharmacological agent suspended in air or other carrier gas, which may be delivered by insufflation from an inhaler device, for example.

For solutions used in making aerosols, the preferred range of concentration of the pharmacological agent is 0.1-100 milligrams (mg)/milliliter (mL), more preferably 0.1-30 mg/mL, and most preferably, 1-10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, DRUG DELIVERY TO THE RESPIRATORY TRACT, Ellis Horwood (1987); Gonda (1990) Critical Reviews in Therapeutic Drug Carrier Systems 6:273-313; and Raeburn et al. (1992) J. Pharmacol. Toxicol. Methods 27:143-159.

Solutions of the pharmacological agent may be converted into aerosols by any of the known means routinely used for making aerosol inhalant pharmaceutical. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

Cell lines and reagents. The NSCLC cell lines A549 and H460 were purchased from American Type Culture Collection (ATCC). Gefitinib-resistant A549 (A549GR) was generated by an intermittent selection method through exposing A549 to a stepwise increased concentration of gefitinib (from 24 µM to 50 µM) for 10 months, which simulates the median time (6-12 months) for the development of acquired resistance of gefinitib in clinical applications (Nguyen et al., 2009; Rho et al., 2009). After each treatment of gefitinib for 48 hrs, the surviving cells were sub-cultured and grew to 70-80% confluence in drug-free medium for the next treatment. The dosages of gefitinib would increase continuously based on the tolerance of A549 cells. Concurrently, gefitinib+0.5 nM LMB-resistant A549 (A549GLR) was generated by treating A549 with 0.5 nM LMB as well as the same concentration and exposure time of gefitinib as A549GR. A549 (within five passages), A549GR, and A549GLR were cultured in RPMI 1640 medium (Thermo scientific, Logan, Utah) containing 5% fetal bovine serum (FBS) (Invitrogen, Carlsbad, Calif.), 100 U/mL penicillin, and 100 µg/mL streptomycin in 5% $CO_2$ incubator at 37° C. For all the in vitro studies, the established A549GR and A549GLR were cultured in drug-free medium for at least 1 week to eliminate the effects of gefitinib and/or LMB.

Gefitinib (>98%) was purchased from Santa Cruz Biotechnology (Santa Cruz, Calif.) and LMB (1 mM) was purchased from LC labs (Woburn, Mass.). Afatinib (>99%) was obtained from Selleckchem (Houston, Tex.). The stocks of gefitinib (10 mM), afatinib (10 mM), and LMB (10 µM) were diluted to the required concentrations immediately before use in the growth media. Primary antibodies including EGFR, phospho-EGFR(Tyr1068), p44/42 MAPK (Erk1/2), phospho-p44/22 MAPK (Erk1/2)(Thr202/Tyr204), Akt, phospho-Akt(Ser473), phospho-STAT3(Ser727), MET (D1C2), HER2/ErbB2 (D8F12), p21, survivin, E-cadherin, vimentin, and α-tubulin were purchased from Cell Signaling Technology (Danvers, Mass.). Twist1 antibody was purchased from Sigma-Aldrich (St. Louis, Mo.). Horseradish peroxidase (HRP)-conjugated donkey anti-rabbit IgG, anti-mouse IgG, and chemiluminescence kit were purchased from Cell Signaling Technology. Radioimmunoprecipitation assay (RIPA) lysis buffer was obtained from Santa Cruz Biotechnology.

Cell viability assay. Cell viability was evaluated by the MTT assay as described previously (Shao et al., 2011; Lu et al., 2012; Gao et al., 2015). Briefly, based on the cytotoxicity of LMB observed in this study and in previous reports by the present inventors (Shao et al., 2011; Lu et al., 2012; Gao et al., 2015), 0.5 nM LMB was selected for co-treatment. The synergistic effect of gefitinib and LMB was evaluated by comparing to vehicle controls for gefitinib treatments or LMB (0.5 nM) for gefitinib+LMB treatments as described in the inventors' previous studies (Gao et al., 2015; Lu et al., 2015). Experiments were repeated independently three times.

Analysis of cell cycle by flow cytometry. Based on the cell viability assay, a total of six groups of A549 with different treatments for 48 hrs were analyzed, including control, 0.5 nM LMB (LMB), 12 µM gefitinib (Gefitinib12), 24 µM gefitinib (Gefitinib24), 12 µM gefitinib+0.5 nM LMB (Gefitinib12+LMB), and 24 µM gefitinib+0.5 nM LMB (Gefitinib24+LMB). Cells were stained with Guava Cell Cycle Reagent (Millipore, Billerica, Mass.) and run on a Guava EasyCyte™ Flow Cytometer (Millipore) as previously described (Lu et al., 2012). Each sample was run in triplicate and each experiment was repeated three times.

Wound healing assay, anchorage-independent growth assay, and transwell invasion assay. The wound healing assay (scratch assay) was performed to examine and compare the migration abilities of A549, A549GR, and A549GLR as previously described (Gao et al., 2015). Photographs of the wounded area were taken at the time of wounding and thereafter at 6, 12, 24, and 48 hrs to determine the wound closure rate.

Anchorage-independent growth was determined by agar colony formation assay following a previous protocol (Gao et al., 2015; Lv et al., 2015). Colonies were stained using 0.005% crystal violet and the number of colonies/areas (six randomly selected areas/well) were measured by an image analyzer under a microscope.

Transwell assay was performed using cell culture inserts of 6.5 mm diameter (Corning incorporated, New York, USA) as described previously (Wang et al., 2016). Briefly, the 8-µm pore size filters were coated with 100 µL of 1 mg/mL Matrigel (BD Biosciences, San Jose, Calif.) at 4° C. and the Matrigel layers were solidified at 37° C. for 1 hr. A total of 500 µL culture medium was added to the lower champers, and 200 µL of A549, A549GR, and A549GLR cell suspensions ($1 \times 10^5$ cells/mL) were added into the upper chambers. The invasion lasted for 16 hrs at 37° C. in dark. The cells migrated through the filters were fixed with 95% ethanol and stained with 0.005% crystal violet for 20 min at room temperature. Pictures of five random areas in each insert were photographed by a microscopy and the number of cells that had reached the underside of the inserts was counted.

Western blot analyses. The same six treatment groups of A549 exposing to gefitinib and/or LMB for 48 hrs as described in the flow cytometry as well as A549, A549GR, and A549GLR were analyzed by Western blot as previously described (Lu et al., 2012; Lv et al., 2015). Relative densitometric digital analysis for bands of targeted proteins was determined using Image J and normalized by the intensity of the housekeeping gene, α-tubulin.

Bio-Plex multiplex immunoassay for detection of phosphorylated MAP kinases. p-ATF2(T71), p-Erk(T202/Y204), p-HSP27(S78), p-MEK1(S217/221), p-p53(S15), p-p90 RSK (S380), p-STAT3(S727), p-JNK(T183/Y185), and p-p38MAPK(T180/Y182) in A549, A549GR, and A549GLR were determined by Bio-Plex Pro™ Cell Signaling MAPK Panel (9-plex #LQ00000S6KL81S). The assay was performed according to the manufacturer's protocol. The amounts of nine molecules and glyceraldehyde 3-phosphate (GAPDH, as an internal control) were determined by fluorescence signals of the multiplex assay suspensions in a MAGPIX (Luminex, Austin, Tex.). In order to exclude background noise, only the molecules with fluorescent signal over 100, including p-ATF2, p-MEK1, and p-STAT3, were selected for characterizations.

PCR and T790M mutation analyses. Genomic DNAs from A549, A549GR, and A549GLR were isolated using a DNeasy Blood & Tissue Kit (Qiagen, Valencia, Calif.). EGFR exon 20 was amplified by PCR according to the method established previously (Conde et al., 2006). The PCR products were electrophoresed on 2% agarose gel, purified by QIAquick PCR Purification Kit (Qiagen), and sequenced. The PCR primers and the sequencing primer for EGFR exon 20 were included in Table 2.

Total RNA was isolated from A549, A549GR, and A549GLR using the RNeasy Plus Mini Kit (Qiagen) following the manufacturer's protocol. One-step RT-PCR Kit with SYBR green was used for amplification of total mRNA (75 ng) following the manufacturer's protocol (BioRad, Hercules, Calif.) and the inventors' previous studies (Lu et al., 2012; Gao et al., 2015; Lv et al., 2015). For MET, METFR (endogenous control for MET), HER2, and EFTUD2 (endogenous control for HER2), 75 ng of genomic DNA was amplified using SYBR Green Supermix (BioRad). Experiment was performed in triplicate for each group. The PCR primers were included in Table 2, SEQ ID NOS: 1-33, respectively.

TABLE 2

PCR Primers for amplifications of DNA and mRNA

| Primers | Sequence 5'-3' | SEQ ID NO. |
| --- | --- | --- |
| DNA | | |
| EGFR exon20-F | GATCGCATTCATGCGTCTTC | 1 |
| EGFR exon20-R | TCCCCATGGCAAACTCTTGC | 2 |
| EGFR exon20 (Sequencing) | CGCATTCATGCGTCTTCACC | 3 |
| MET-F | CCATCCAGTGTCTCCAGAAGTG | 4 |
| MET-R | TTCCCAGTGATAACCAGTGTGTAG | 5 |
| MTHFR-F | CCATCTTCCTGCTGCTGTAACTG | 6 |
| MTHFR-R | GCCTTCTCTGCCAACTGTCC | 7 |
| HER2/ErbB2-F | ACAACCAAGTGAGGCAGGTC | 8 |
| HER2/ErbB2-R | GTATTGTTCAGCGGGTCTCC | 9 |

TABLE 2-continued

PCR Primers for amplifications of DNA and mRNA

| Primers | Sequence 5'-3' | SEQ ID NO. |
| --- | --- | --- |
| EFTUD2-F | GGTCTTGCCAGACACCAAAG | 10 |
| EFTUD2-R | TGAGAGGACACACGCAAAAC | 11 |
| mRNA | | |
| EGFR-F | CTGCGTCTCTTGCCGGAATG | 12 |
| EGFR-R | TTGGCTCACCCTCCAGAAGG | 13 |
| STAT3-F | TTGCCAGTTGTGGTGATC | 14 |
| STAT3-R | AGACCCAGAAGGAGAAGC | 15 |
| Survivin-F | TGCCCCGACGTTGCC | 16 |
| Survivin-R | CAGTTCTTGAATGTAGAGATGCGGT | 17 |
| E-cadherin-F | CGGGAATGCAGTTGAGGATC | 18 |
| E-cadherin-R | AGGATGGTGTAAGCGATGGC | 19 |
| N-cadherin-F | CCTTTCACTGCGGTACAGTG | 20 |
| N-cadherin-R | GATCCAGGGGCTTTGTCACC | 21 |
| Vimentin-F | CTTGAACGGAAAGTGGAATCCT | 22 |
| Vimentin-R | GTCAGGCTTGGAAACGTCC | 23 |
| Twist1-F | GGCTCAGCTACGCCTTCTC | 24 |
| Twist1-R | TCCTTCTCTGGAAACAATGACA | 25 |
| Snail1-F | CGCGCTCTTTCCTCGTCAG | 26 |
| Snail1-R | TCCCAGATGAGCATTGGCAG | 27 |
| CD24-F | TGCTCCTACCCACGCAGATT | 28 |
| CD24-R | AGACCACGAAGAGACTGGCT | 29 |
| CD44-F | CCCAGATGGAGAAAGCTCTG | 30 |
| CD44-R | GTTGTTTGCTGCACAGATGG | 31 |
| CD133-F | GGGATGGTGCCTTGAGTGA | 32 |
| CD133-R | GTTCCTGGGCAGAAGAGGAG | 33 |

Statistical analyses. Factorial ANOVA was performed to test the effects of gefitinib and/or LMB concentrations and incubation times on cell viability. Prism 6.0 was used to calculate the 50% inhibitory concentrations (IC50s). One-way ANOVA was used to determine the difference in the analytical results of flow cytometry, qRT-PCR, Western bot, wound healing assay, anchorage-independent growth assay, transwell invasion assay, and Bio-Plex multiplex immunoassay among groups followed by a Fisher's LSD test. Differences with $p<0.05$ were considered statistically significant.

Figure 1B:
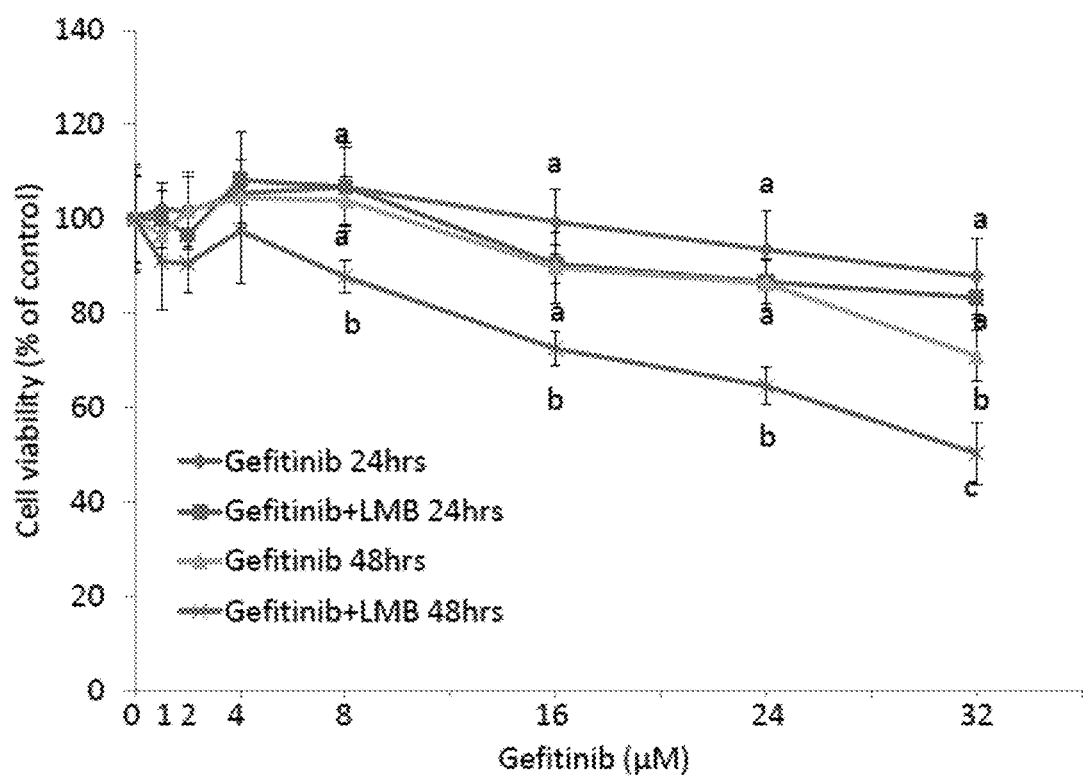

Cytotoxicity of co-treatment of gefitinib and/or LMB in A549 and H460. As shown in FIG. 1A, the simultaneous treatments of gefitinib (0-32 µM) and LMB (0.5 nM) showed synergistic cytotoxic effect on A549 as compared to gefitinib alone at both 24 and 48 hrs ($p<0.05$, n=3). The IC50 of gefitinib at 48 hrs was 32.0±2.5 µM while it was significantly reduced to 25.0±2.1 µM with the combination of 0.5 nM LMB (p<0.05, n=3). The significant synergistic cytotoxic effect from co-treatment of 0.5 nM LMB with gefitinib was also confirmed in H460 cell line (FIG. 1B).

Figure 1C:
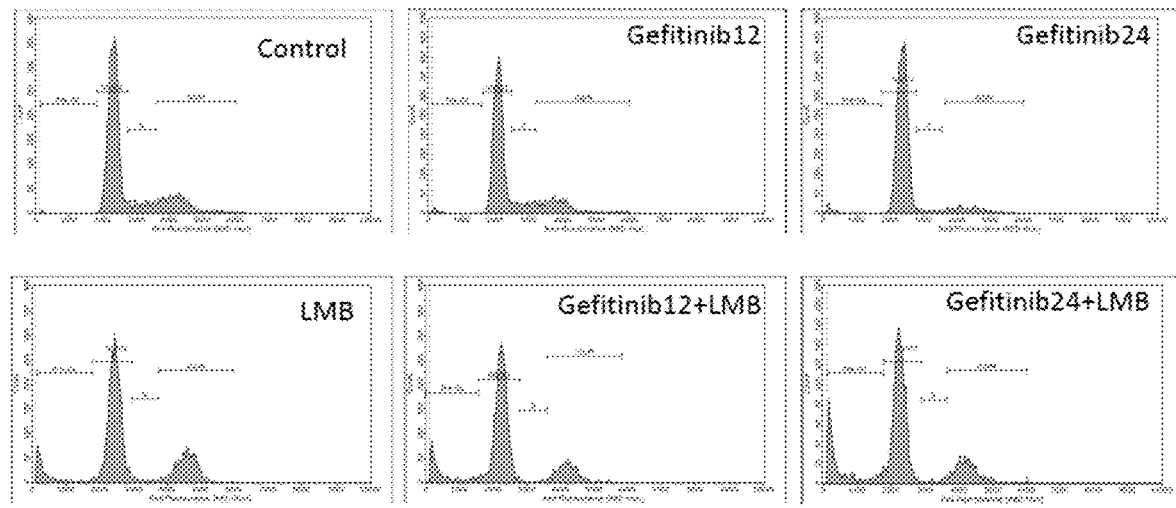

Flow cytometry analyses of cell cycle distributions in A549 treated by gefitinib and/or LMB. Cell cycle analyses were conducted to further investigate the mechanism of the synergistic effect of gefitinib and LMB on the A549 cell proliferation inhibition. Table 1 and FIG. 1C showed that the gefitinib+LMB co-treatments caused a decreased accumulation of A549 in G0/G1 and S phases compared with gefitinib treatment alone. In contrast, LMB, Gefitinib12+LMB, and Gefitinib24+LMB resulted in a dramatic increased accumulation of A549 in the pre-G1 phase compared to control, Gefitinib12, and Gefitinib24, respectively (p<0.05). A much higher number of pre-G1 phase cells in Gefitinib24+LMB represents a higher apoptotic population than LMB or gefitinib alone, which further validated the synergistic effect of gefitinib+LMB detected by the MTT assay.

TABLE 1

Effects of gefitinib and/or LMB on cell cycles of A549

| Group | Cell cycle (%) | | | |
|---|---|---|---|---|
| | Pre-G1 | G0/G1 | S | G2/M |
| Control | 1.3 ± 1.4 [a] | 67.9 ± 6.3 [a] | 10.0 ± 2.8 [a] | 20.5 ± 2.4 [a] |
| LMB | 13.5 ± 2.7 [b] | 57.9 ± 3.1 [b] | 3.6 ± 1.2 [b] | 24.4 ± 0.6 [b] |
| Gefitinib12 | 2.1 ± 0.4 [a] | 68.0 ± 2.9 [a] | 9.7 ± 2.4 [a] | 19.9 ± 2.2 [a] |
| Gefitinib12 + LMB | 14.9 ± 4.3 [b,c] | 63.5 ± 3.2 [a] | 1.6 ± 0.3 [b,c] | 19.2 ± 1.6 [a] |
| Gefitinib24 | 4.0 ± 1.3 [b] | 84.0 ± 0.9 [b] | 3.4 ± 0.3 [b] | 7.9 ± 0.6 [b] |
| Gefitinib24 + LMB | 23.7 ± 3.1 [b,c] | 56.3 ± 3.5 [b,c] | 2.3 ± 0.3 [b,c] | 16.7 ± 1.9 [a,c] |

Data are represented as mean ± SD (n = 3). Mean values within the same column containing different superscript letters indicates significance among the treatment groups analyzed by one-way ANOVA followed by a Fisher's LSD test ($p_c$ < 0.05). Values bearing the letter [a] indicate no significant differences compared with control, those labels [b] denote a significant difference when compared with the control, and [c] denotes a significant difference when Gefitinib + LMB is compared with Gefitinib alone.

Figure 2A:
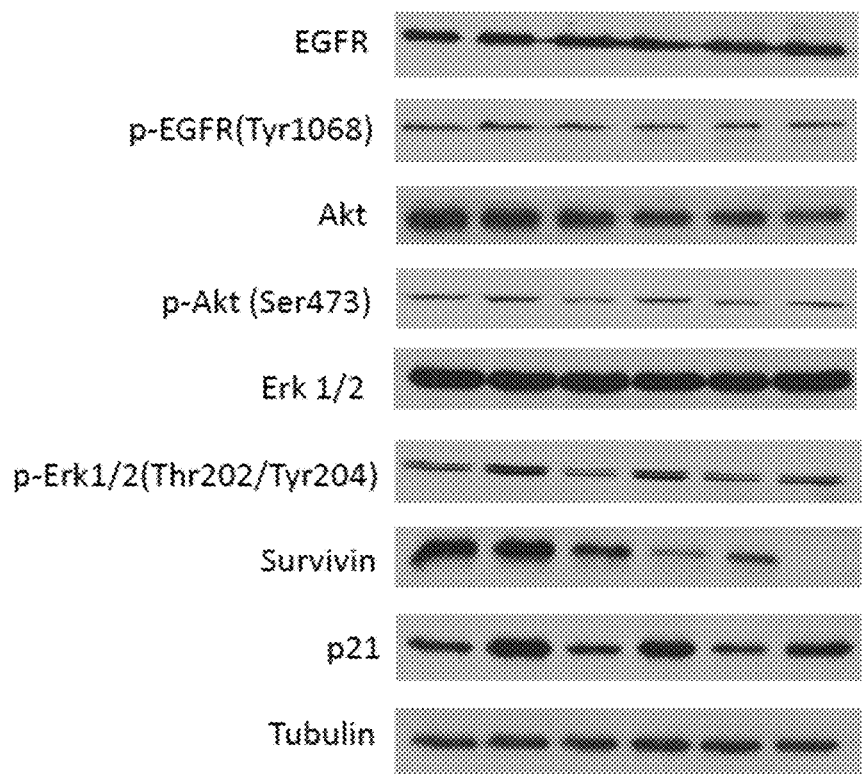
FIG. 2A shows a Western blot analyses of protein expressions in A549 after gefitinib and/or LMB treatment.
Figure 2B:
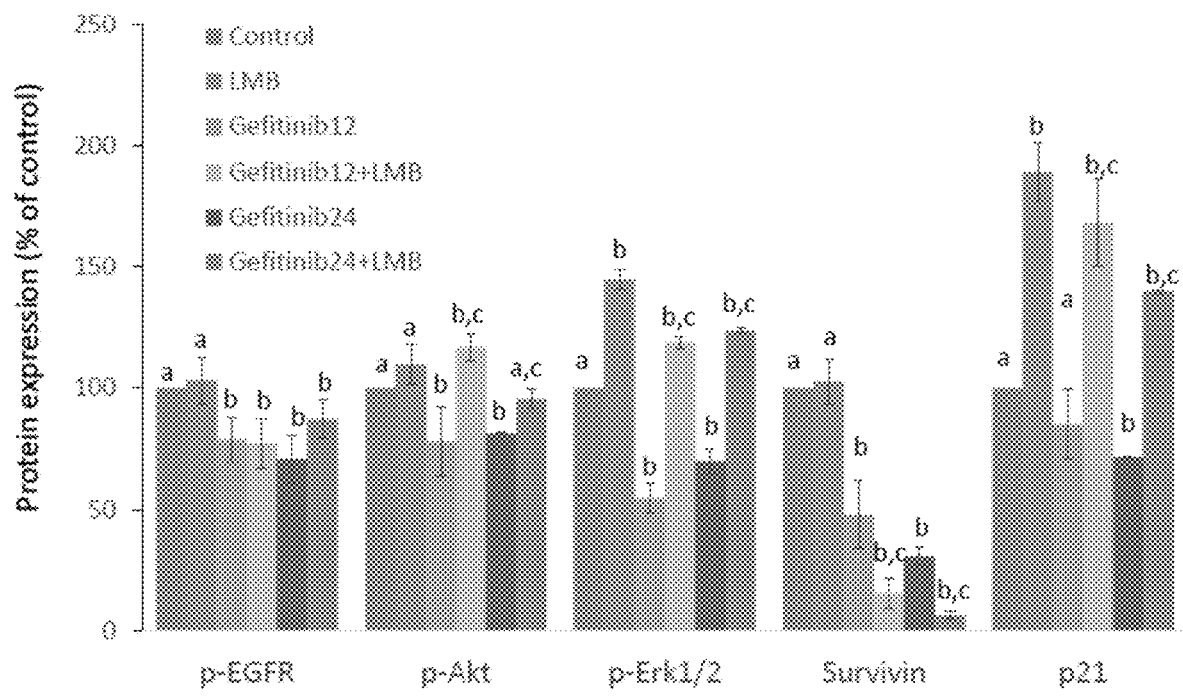
FIG. 2B is a graph that shows the relative protein intensities of p-EGFR(Tyr1068), p-Akt(Ser473), p-Erk1/2(Thr202/Tyr204), survivin, and p21 as compared to the control after normalized by the intensity of α-tubulin. The intensity of each band was quantified using ImageJ software. Data are means±SD, n=3. Mean values within the same column containing different superscript letters indicates a significant difference among the treatment groups (p<0.05). Values bearing the letter "a" indicate no significant differences compared with control, those labeled "b" denote a significant difference when compared with the control, and "c" denotes a significant difference when gefitinib+LMB is compared with gefitinib alone. LMB: 0.5 nM LMB, Gefitinib12: 12 µM gefitinib, and Gefitinib24: 24 µM gefitinib.

Western blot analyses of EGFR signaling and survival pathways in A549 after gefitinib and/or LMB treatments. In order to further investigate the synergistic mechanism of gefitinib and LMB treatment in A549, the expression levels of EGFR, p-EGFR(Tyr1068), Erk1/2, p-Erk1/2(Thr202/Tyr204), Akt, p-Akt(Ser473), survivin, and p21 were evaluated. As shown in FIGS. 2A & 2B, A549 treated with 0.5 nM LMB plus gefitinib or gefitinib alone had a decreased p-EGFR(Tyr1068) expressions compared with controls (p<0.05). p-Akt (Ser473) was inhibited in a dose-response manner by gefitinib treatments, but it was enhanced by gefitinib+LMB co-treatments compared with gefitinib alone (p<0.05) (FIGS. 2A & 2B). A549 treated by gefitinib+LMB had a higher expression of p-Erk1/2(Thr202/Tyr204) than A549 treated by gefitinib alone (p<0.05, FIGS. 2A & 2B). In contrast, the changes in the expressions of EGFR, Akt, and Erk1/2 were not significant between gefitinib and gefitinib+LMB co-treatments (FIGS. 2A & 2B), though Akt was downregulated dose-responsibly in A549 treated by gefitinib or gefitinib+LMB. The relative protein expression levels of Akt were 100.0±0, 86±2, 86±14, 57±3, 70±9, and 61±6 in the control, LMB, Gefitinib12, Gefitinib12+LMB, Gefitinib24, and Gefitinib24+LMB, respectively. Additionally, the synergistic effect between gefitinib and LMB was manifested by the observation that gefitinib+LMB co-treated A549 had a significant downregulation of survivin than gefitinib-treated A549 (p<0.05, FIGS. 2A & 2B). Finally, it was also found that A549 treated with LMB had a dramatically increased p21 expression compared with the control (p<0.05), which may explain why the p21 levels in A549 treated with gefitinib+LMB were significantly higher than the cells treated with gefitinib alone (p<0.05, FIGS. 2A & 2B).

Figure 3A:
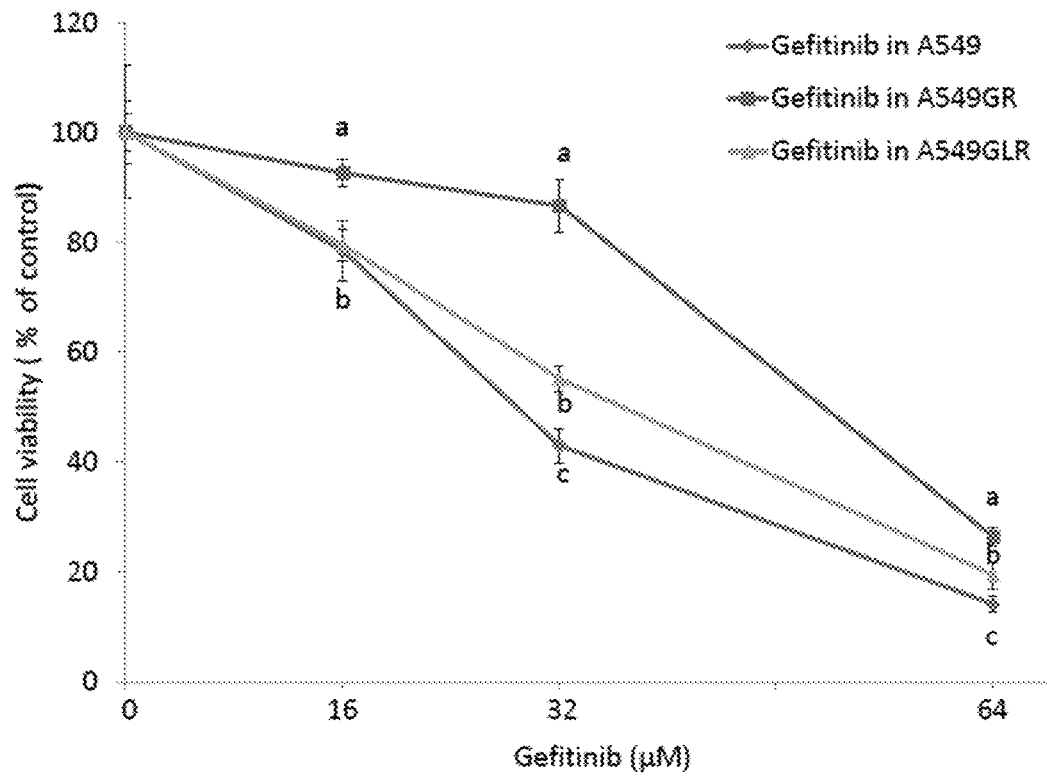
FIGS. 3A and 3B show the cytotoxic effects of (FIG. 3A) gefitinib or (FIG. 3B) afatinib on A549, A549GR, and A549GLR. Cytotoxic effects of gefitinib or afatinib on the cell viability of A549, A549GR, and A549GLR were determined by the MTT assay. Data are expressed as the percentage by comparing to vehicle controls. Values are represented as mean±SD, n=6. Mean values at the same concentration containing different letters indicate a significant difference among the treatment groups analyzed by a one-way ANOVA followed by a Fisher's LSD test (p<0.05).
Figure 3B:
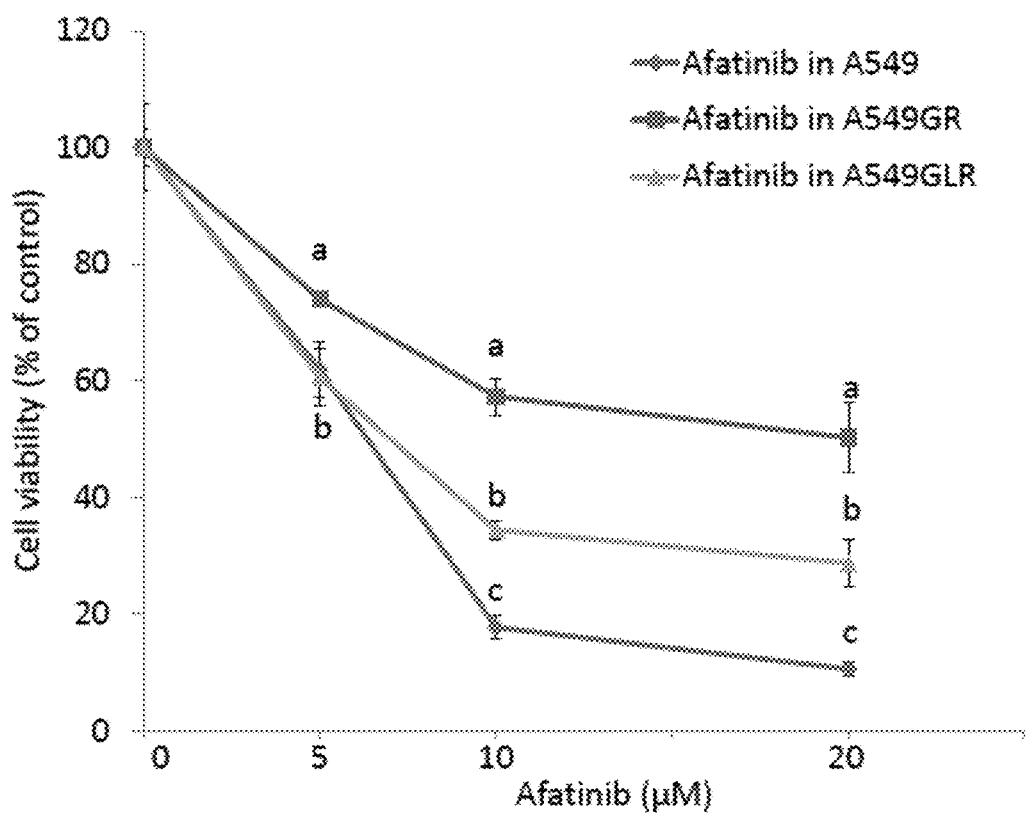

Cytotoxicity of gefitinib or afatinib in A549, A549GR, and A549GLR. As shown in FIG. 3A, IC50s of gefitinib in A549GR and A549GLR at 48 hrs were 53.0±3.0 and 37±2.8 µM, respectively. Therefore, 0.5 nM LMB treatment for 10 months could significantly delay the development of gefitinib resistance in A549, which was demonstrated by the IC50 difference between A549GR and A549GLR (p<0.05, n=3). The cross-resistance of A549GR and A549GLR to the second generation EGFR TKI afatinib was further investigated. FIG. 3B showed that IC50s of afatinib in A549, A549GR, and A549GLR were 6.0±1.2, 20.0±2.7, and 8.0±1.5 µM, respectively. The acquired resistance in both A549GR and A549GLR against gefitinib stably existed for months after gefitinib and/or LMB were removed from medium (data not shown).

Figure 4A:
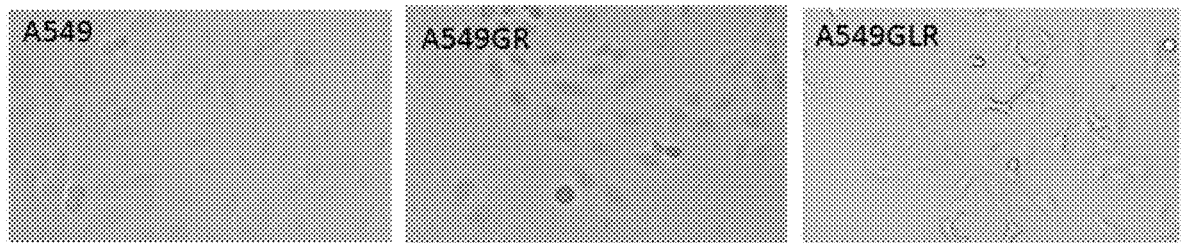
FIGS. 4A to 4G show the characterizations of A549, A549GR, and A549GLR.

Characterizations of A549, A549GR, and A549GLR by morphology, anchorage-independent growth assay, wound healing assay, and transwell invasion assay. Over 10 months exposure to gefitinib with increasing concentrations, A549 progressed gradually to a spindle-shaped morphology (FIG. 4A), which is consistent with the shape description of A549GR in a previous study (Rho et al., 2009). Interestingly, compared with A549GR, A549GLR elongates more to an asterisk-like morphology, which has never been reported before (FIG. 4A).

Figure 4B:
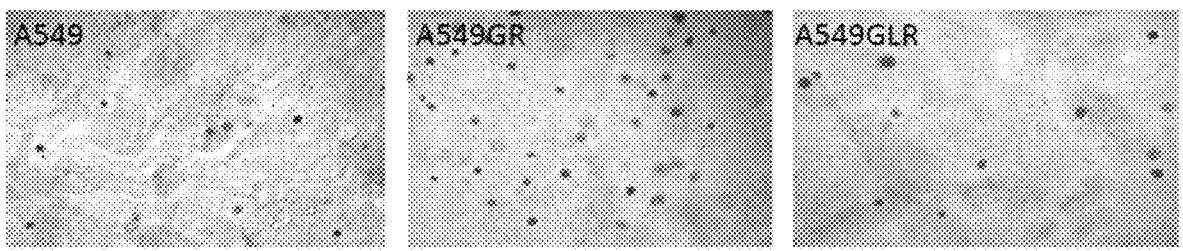
Figure 4C:
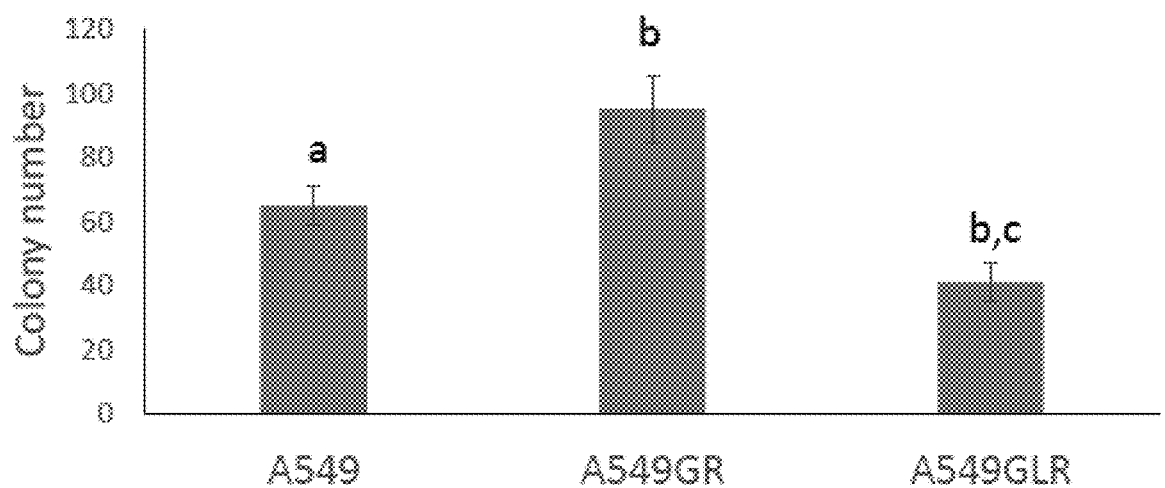
Figure 4D:
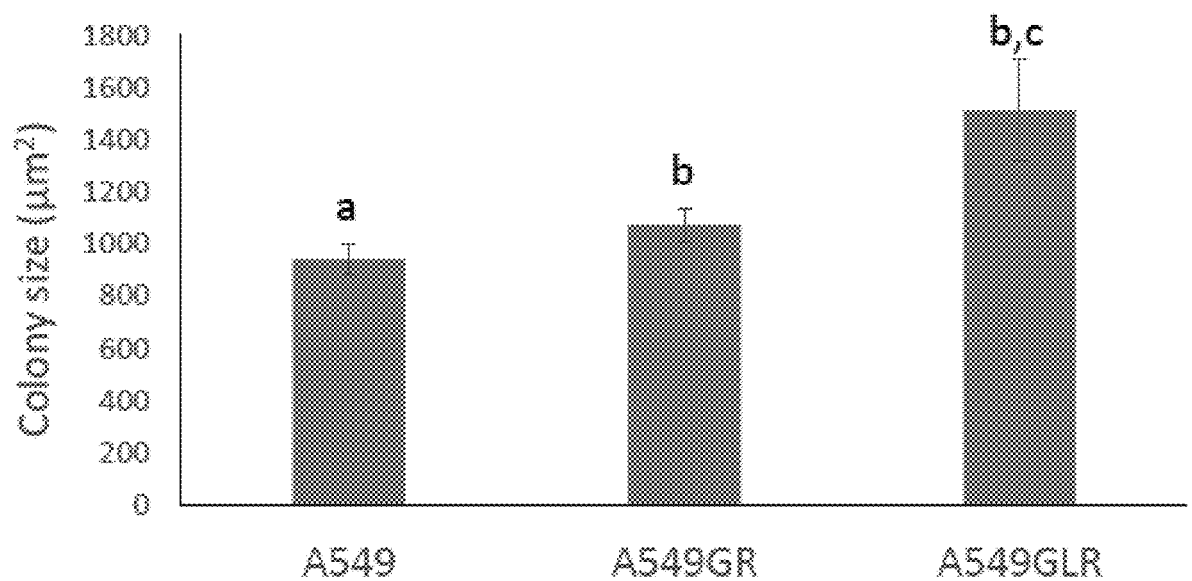

To compare the tumorigenic potential of A549GR and A549GLR, anchorage-independent growth assay was implemented. As shown in FIGS. 4B & 4D, a significant increase in colony size (µm$^2$) was found in A549GR and A549GLR compared to A549 (p<0.05, 940±58 in A549, 1074±62 in A549GR, and 1512±193 in A549GLR). However, FIG. 4C showed a significant increase in colony number was observed in A549GR compared to A549, while a significant decrease in colony number in A549GLR compared to A549 and A549GR (p<0.05, 65±6 in A549, 95±11 in A549GR, and 41±6 in A549GLR).

Figure 4E:
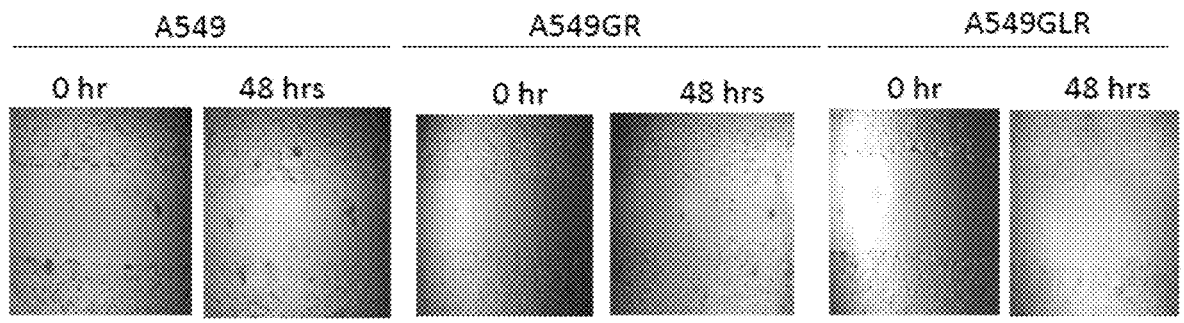
Figure 4F:
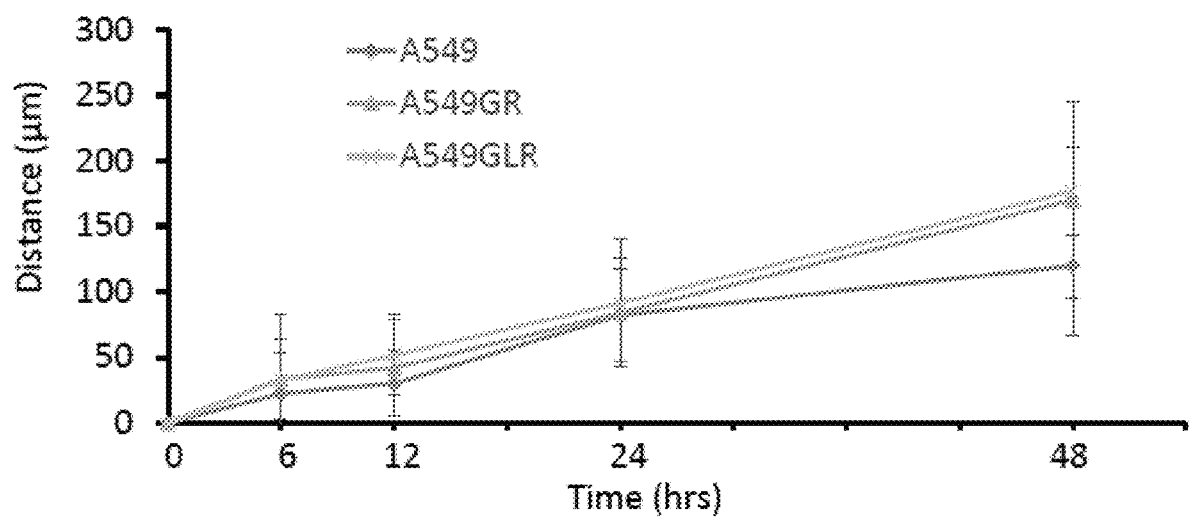
Figure 4G:
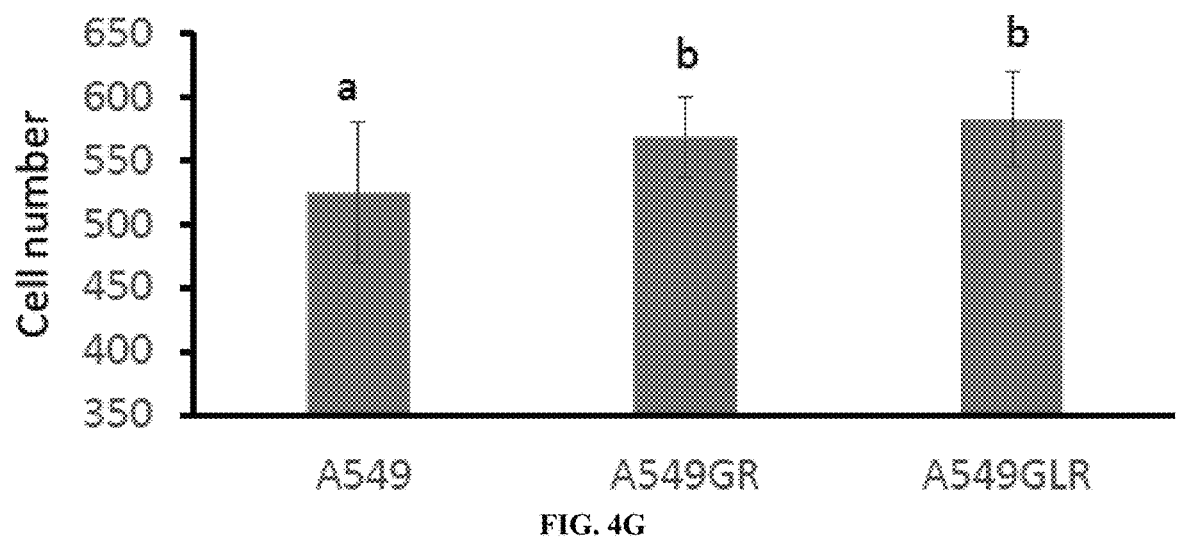

The differences in the migration and invasion abilities of the three cell lines were further examined by wound healing assay and transwell invasion assay. FIGS. 4E & 4F showed that the migration abilities of A549GR and A549GLR are significantly higher than A549 at only 48 hrs (p<0.05). FIG. 4G showed that both A549GR (567±31) and A549GLR (582±37) exhibited higher invasion abilities than A549 (524±55) (p<0.05).

Figure 5A:
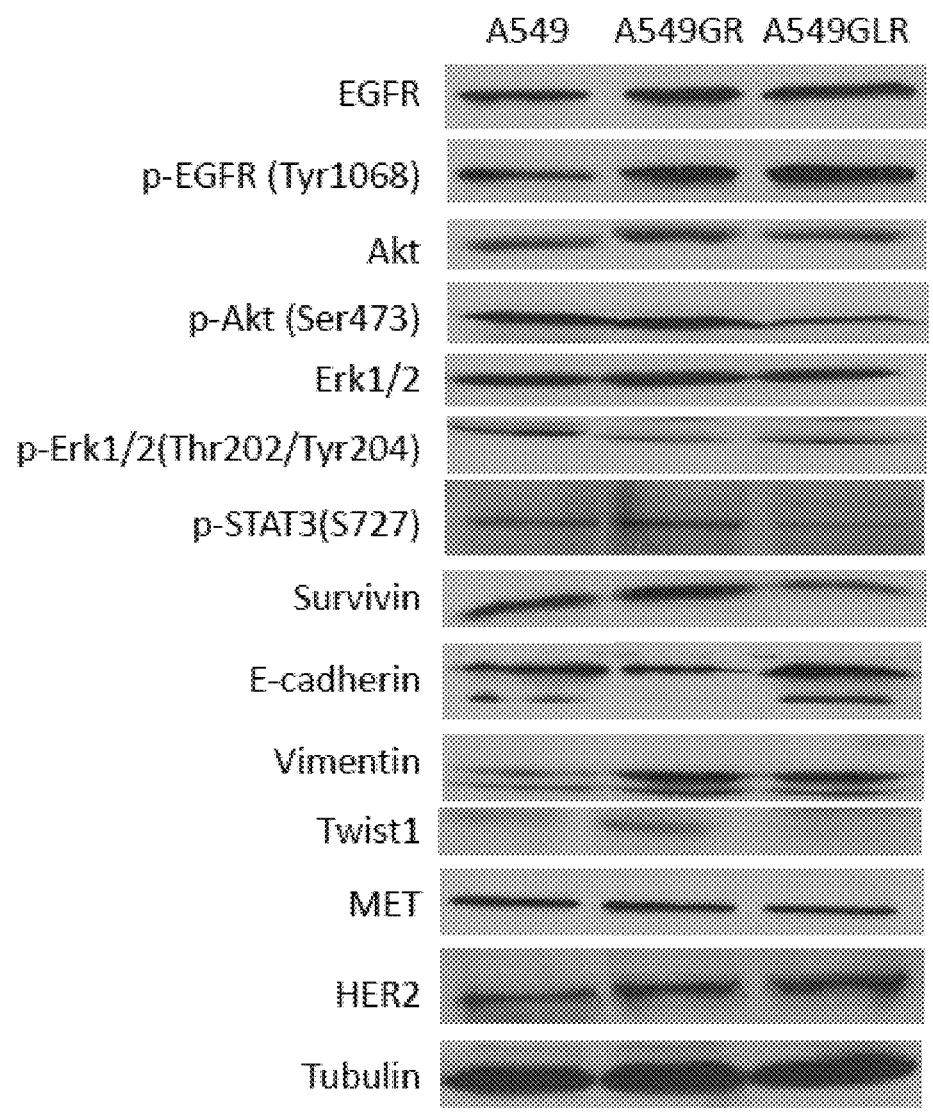
FIGS. 5A and 5F show a protein and gene analyses in A549, A549GR, and A549GLR, respectively.
Figure 5B:
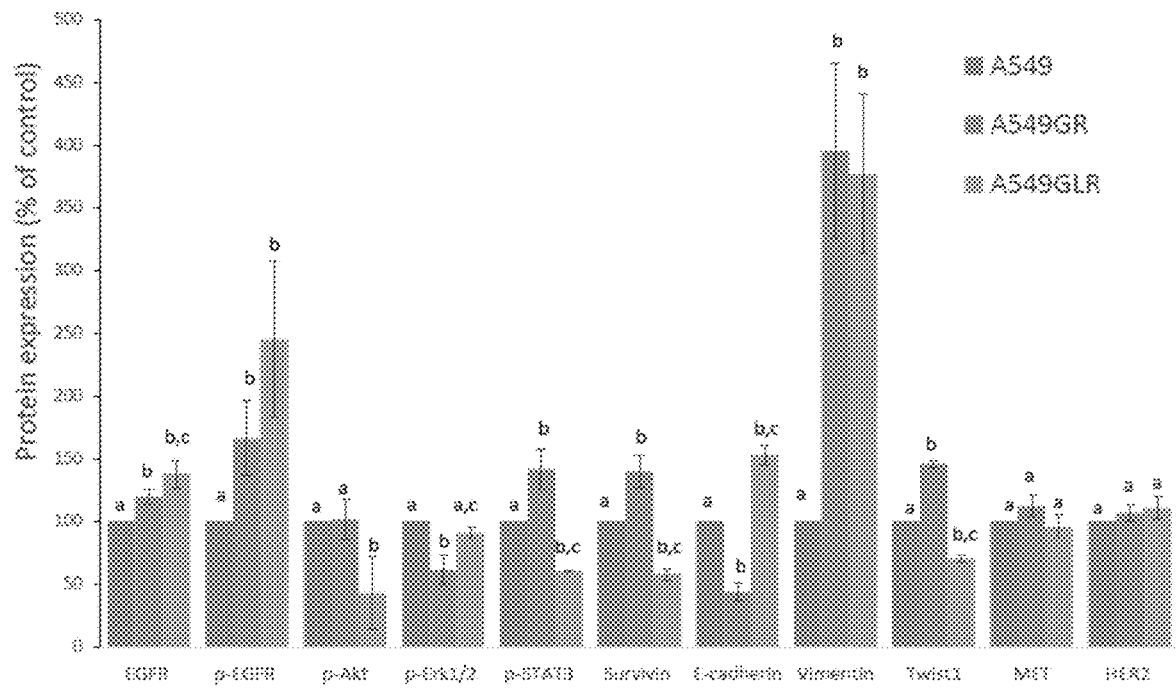
(FIG. 5B) The relative protein intensities of EGFR, p-EGFR(Tyr1068), p-Akt(Ser473), p-Erk1/2(Thr202/Tyr204), p-STAT3(S727), survivin, E-cadherin, vimentin, Twist1, MET, and HER2 as compared to A549 after normalized by the intensity of α-tubulin. The intensity of each band was quantified using ImageJ software. Data are means±SD, n=3.
Figure 5C:
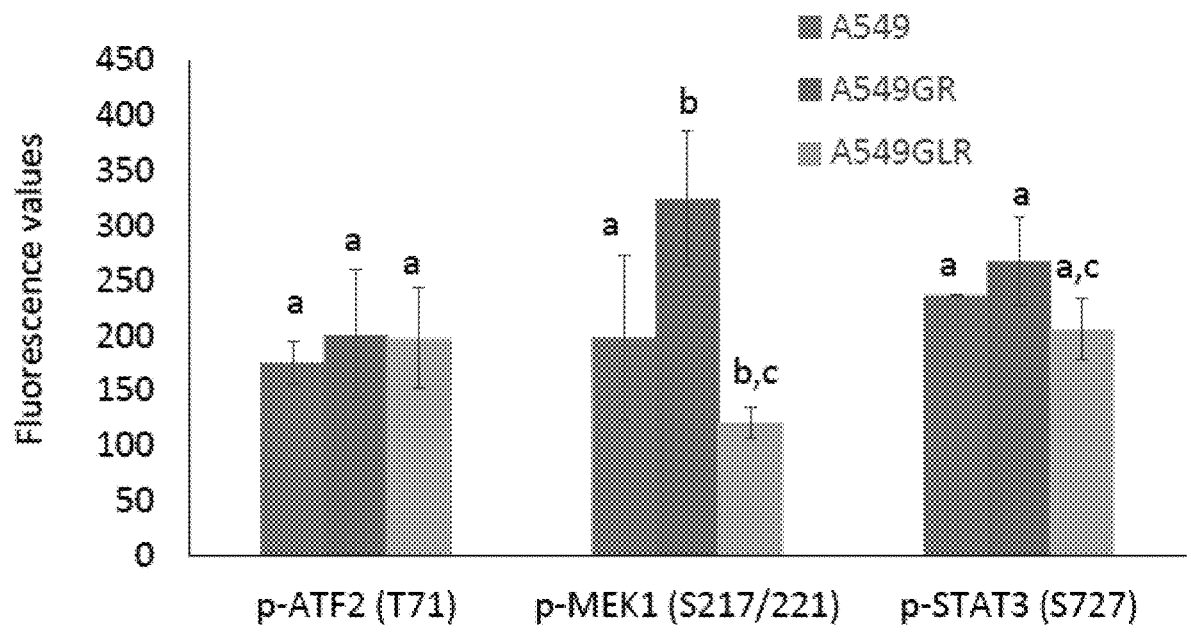
(FIG. 5C) Bio-Plex multiplex immunoassay for detections of p-ATF2, p-MEK1, and p-STAT3 in A549, A549GR, and A549GLR.

Protein analyses of EGFR signaling pathways and EMT markers in A549, A549GR, and A549GLR. The phenotypes of A549, A549GR, and A549GLR were characterized by comparing the protein expressions of the EGFR pathway, EMT biomarkers (E-cadherin, vimentin, and Twist1), as well as HER2/ErbB2 and MET. FIGS. 5A & 5B showed that the expressions of both EGFR and p-EGFR(Tyr1068) were significantly higher in A549GR and A549GLR than A549 ($p<0.05$). p-Akt(Ser473), p-STAT3(S727), and survivin were significantly downregulated in A549GLR compared with A549 and A549GR, while p-Erk1/2(Thr202/Tyr204) was significantly downregulated in A549GR compared with A549 and A549GLR ($p<0.05$, FIGS. 5A & 5B). There were no significant differences of Akt and Erk1/2 expressions among A549, A549GR, and A549GLR (FIGS. 5A & 5B). Bio-Plex multiplex immunoassays (FIG. 5C) further showed that p-MEK1 and p-STAT3 in A549GLR were significantly suppressed compared with A549GR ($p<0.05$).

As for EMT biomarkers, a typical EMT change was observed in A549GR including a significant decrease in E-cadherin while a remarkable increase in vimentin compared with A549 ($p<0.05$, FIGS. 5A & 5B). However, simultaneous elevated expressions of E-cadherin and vimentin were found in A549GLR compared with A549 ($p<0.05$, FIGS. 5A & 5B), which is a new pattern of EMT biomarker change that has not been reported before. Additionally, Twist1, a negative regulator of E-cadherin (Peinado et al., 2007), was significantly increased in A549GR compared with A549 and A549GLR ($p<0.05$, FIGS. 5A & 5B). There were no significant differences of HER2/ErbB2 and MET expressions among A549, A549GR, and A549GLR (FIGS. 5A & 5B).

Figure 5D:
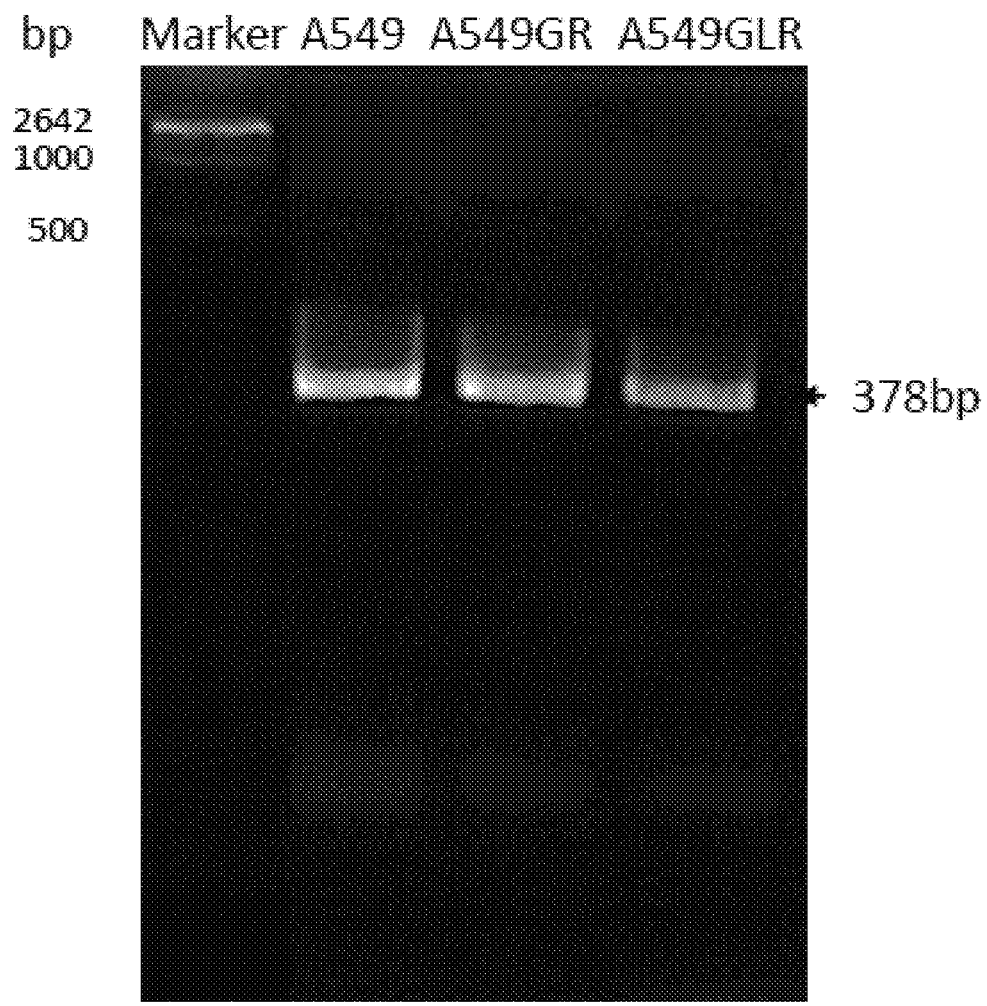
(FIG. 5D) 2% agarose gels shows 378 bp bands of EGFR exon 20 PCR products amplified from A549, A549GR, and A549GLR.
Figure 5E:
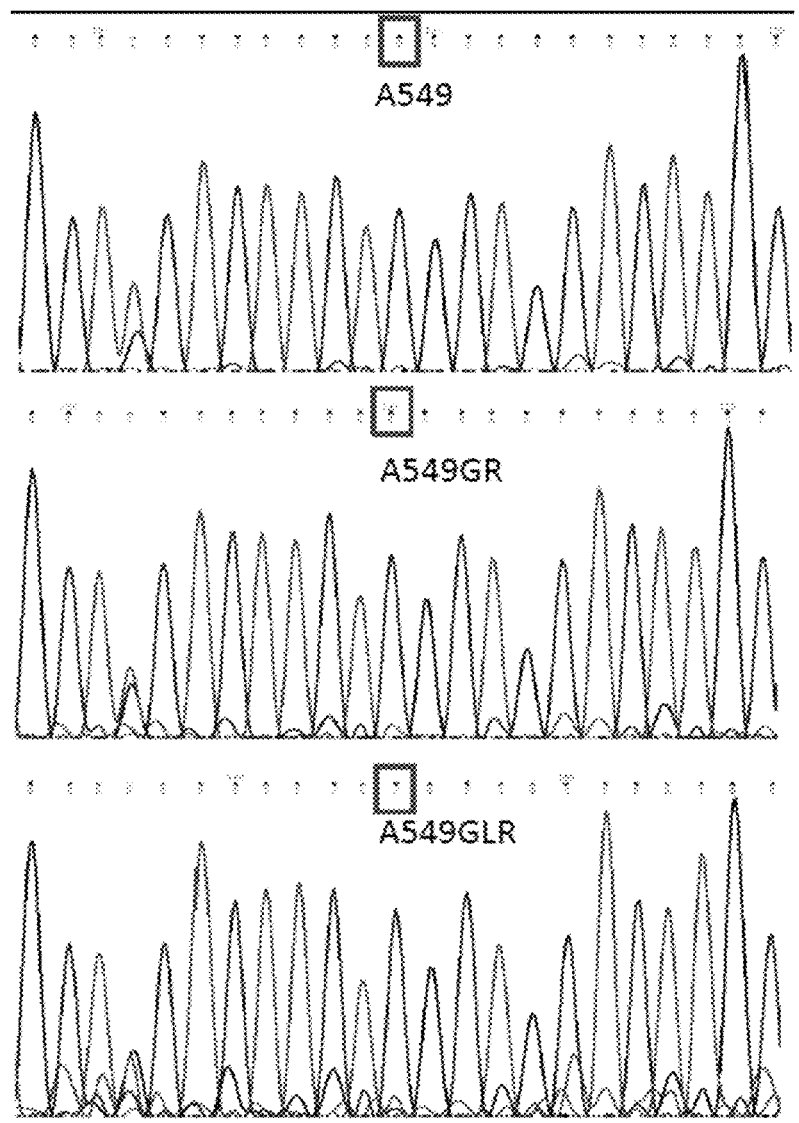
(FIG. 5E) DNA sequencing for EGFR exon 20 of A549, A549GR, and A549GLR. The typical EGFR TKI resistant T790M mutations (c.2369C>T) were not found in exon 20 of either A549GR or A549GLR.
Figure 5F:
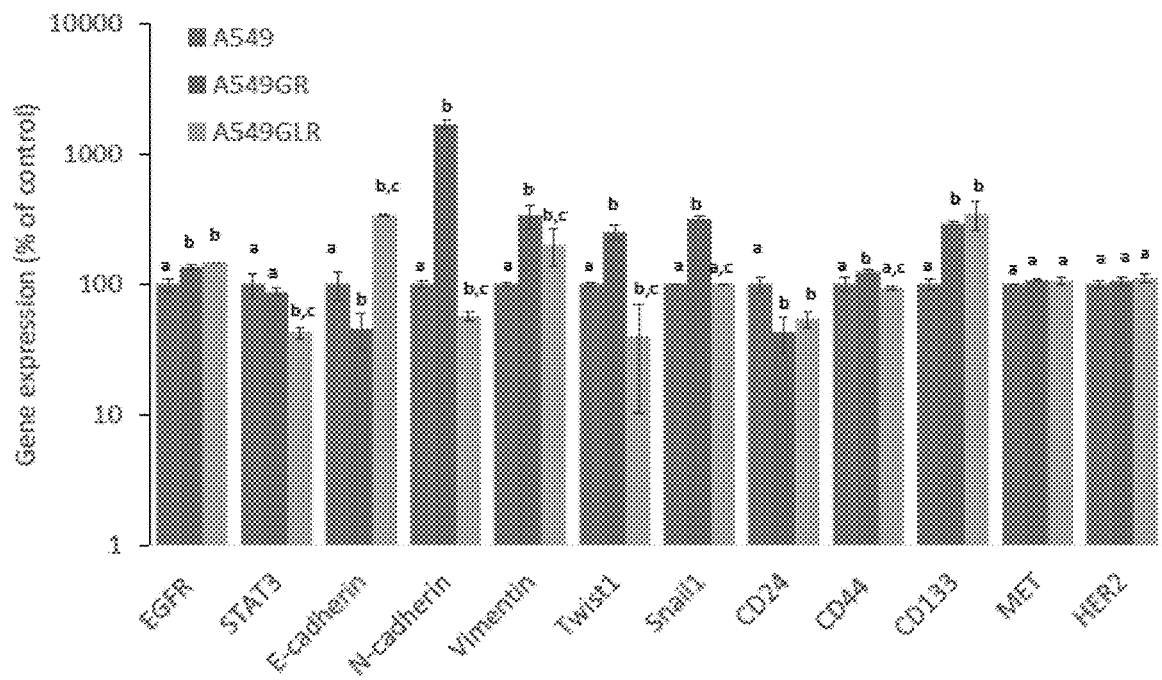

Gene analyses in A549, A549GR, and A549GLR. The 378 bp bands on the 2% agarose gel (FIG. 5D) validated the amplifications of EGFR exon 20 by conventional PCR. The sequence analyses of PCR products of EGFR exon 20 demonstrated there were no EGFR TKI resistant T790M mutation in both A549GR and A659GLR (FIG. 5E). The qRT-PCR results (FIG. 5F) revealed a significantly increased gene expression of EGFR in A549GR and A549GLR compared with A549 ($p<0.05$). The expression of STAT3 was significantly downregulated in A549GLR compared to A549 and A549GLR ($p<0.05$, FIG. 5F). Among the five EMT markers (E-cadherin, N-cadherin, vimentin, Twist1, and Snail1), E-cadherin was significantly downregulated in A549GR but significantly upregulated in A549GLR compared with A549, while N-cadherin, Twist1, and Snail1, were significantly upregulated in A549GR compared with A549 and A549GLR ($p<0.05$, FIG. 5F). On the other hand, the expressions of vimentin were significantly higher in both A549GR and A549GLR than A549, as well as higher in A549GR than A549GLR ($p<0.05$, FIG. 5F). These results signify the EMT inhibiting function of LMB. Cancer stem cells (CSCs) marker CD24 was significantly downregulated while CD133 was significantly upregulated in A549GR and A549GLR compared with A549 ($p<0.05$, FIG. 5F). However, CD44 was significantly upregulated in A549GR compared with A549 and A549GLR ($p<0.05$, FIG. 5F). There were no significant differences of HER2/ErbB2 and MET expressions among A549, A549GR, and A549GLR (FIG. 5F).

Figure 6:
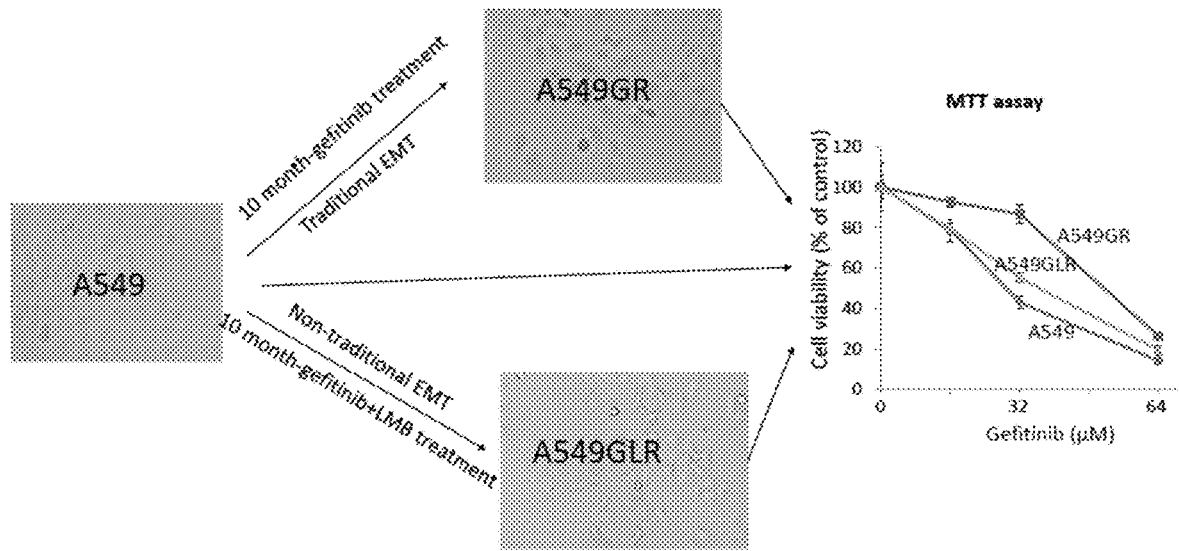
FIG. 6 shows a summary of the results obtained herein, namely, that Leptomycin B shows a synergistic effect with gefitinib on A549 and H460 cells, that Leptomycin B significantly reduced acquired resistance of gefitinib on A549 cells, and that Leptomycin B inhibited epithelial-mesenchymal transition in A549 cells induced by gefitinib.

FIG. 6 shows a summary of the results obtained herein, namely, that Leptomycin B shows a synergistic effect with gefitinib on A549 and H460 cells, that Leptomycin B significantly reduced acquired resistance of gefitinib on A549 cells, and that Leptomycin B inhibited epithelial-mesenchymal transition in A549 cells induced by gefitinib.

In this study, the inventors demonstrate the synergistic effect of LMB on gefitinib-induced cytotoxicity through significantly increasing cell cycle distribution at pre-G1 phase. Further Western blot analyses revealed the distinctive expression patterns of EGFR pathways, survivin, and p21, in A549 treated with gefitinib or gefitinib+LMB for 48 hrs. More importantly, 10 month-gefitinib+LMB co-treatment could significantly reduce the gefitinib-resistance development in A549. It was also observed that the properties of A549GR and A549GLR were different from A549 in terms of colony formation, migration, and invasion capacities. In the colony formation assay, A549GLR had dramatically decreased colony number compared with A549 and A549GR but the colony size of A549GLR was significantly larger than those of A549 and A549GR. In the wound healing and transwell assays, A549GR and A549GLR showed significantly higher migration and invasive abilities than A549. The protein and mRNA profiles of A549, A549GR, and A549GLR showed that the expressions of EGFR pathways, EMT, and CSC biomarkers in A549GR and A549GLR were significantly different.

Many studies, including ours, showed that CRM1 inhibitor LMB could significantly enhance the cytotoxic effects of therapeutic agents and effectively reduce drug resistance in cancer cells (Lu et al., 2012; Gao et al., 2015; Lu et al., 2015). For example, short-term LMB treatment was reported to potentiate the effect of TKI imatinib in treating Bcr-Abl positive leukemia, and combination of imatinib and LMB could effectively induced cell death in imatinib-resistant Ba/F3 cells, which displayed Bcr-Abl amplification or signs of clonal evolution (Kancha et al., 2008; Turner et al., 2014). The inventors' previous studies using both in vitro and in vivo models also showed that the combined treatment between LMB and doxorubicin/cisplatin/epigallocatechin-3-gallate could synergistically increase the chemotherapeutic effects in lung cancer cells (Lu et al., 2012; Cromie and Gao, 2015; Gao et al., 2015). The abilities of LMB leading to remarkable cell growth inhibition in NSCLC cell lines (A549, H522, and H358) but not normal human lung epithelial cells (BEAS-2B) further demonstrated its potential in lung cancer treatment (Shao et al., 2011). In contrast, the study of Wang et al (Wang et al., 2014) showed no synergistic cytotoxic effects between newly developed CRM1 inhibitor (KPT-185) and EGFR TKIs on NSCLC cells. There was also no synergistic effect between KPT-330 and gefitinib observed in A549 and H460 cells in the inventors' prior studies (data not shown).

In a recent study, CRM1 inhibitors, KPT-185 and KPT-330, have showed high efficacy in therapy of KRAS-mutant lung cancer (Kim et al., 2016). However, among many KRAS-mutant NSCLC cell lines studied, A549 is the only exception, which is not responsive to the treatments of KPT-185 or KPT-330. The inventors' previous study also showed that LMB IC50 of A549 at 48 hrs (13.1 nM, p53 wide type) was much higher compared to the other two NSCLC cell lines H522 (5.7 nM, p53-mutant) and H358 (0.5 nM, p53 null) (Shao et al., 2011). It has also been reported that the mutational activation of KRAS contributes to the primary resistance of gefitinib in A549 (Pao et al., 2005b; Chen et al., 2013), and the synergistic effect of gefitinib in combined with other anticancer drugs including vATPase inhibitors (Jin et al., 2015), atorvastatin, aromatase inhibitor anastrozole, MEK inhibitor AZD6244, and cyclooxygenase-2 (COX-2) inhibitor celecoxib on overcoming the primary resistance of A549 (Shen et al., 2012; Chen et al., 2013; Li et al., 2015a; Li et al., 2015b). The inventors' previous study found that the cytotoxic effects of cisplatin were significantly enhanced when used in combination with LMB in both in vitro A549 cells and in vivo mouse xenograft model (Gao et al., 2015). Therefore, combination chemotherapy may be a great opportunity for LMB to regain its application in treating multi-drug resistant A549 cells. Additionally, the findings from this study, together with the recent study showing that KRAS mutated lung cancer cell lines could be druggable though CRM1/XPO1 inhibition (Kim et al., 2016), suggest that combination therapies of EGFR-TKIs with LMB might be selectively applied to lung cancer patients with KRAS mutations.

In the present study, the synergism between gefitinib and LMB in A549 was demonstrated by cytoxicity data obtained from MTT assays, which was further validated by flow cytometry analysis. Previous studies showed that gefitinib induced G0/G1 cell cycle arrest and LMB induced G2/M cell cycle arrest in A549 and H1975 cells (Lu et al., 2012; Sun et al., 2013), which were also observed in cell cycle analyses shown in this study. The co-treatment of gefitinib and LMB caused significant increased proportions of A549 at pre-G1 phase compared with the control and gefitinib alone. The impact of LMB on cell cycle distribution may also be signified by a dramatic higher expression level of p21, which is a cyclin-dependent kinase (Cdk) inhibitor promoting cell cycle arrest, in A549 co-treated with gefitinib+LMB (FIG. 2A). Different from LMB, the study of Wang et al (Wang et al., 2014) showed that KPT-185 arrested NSCLC cells in the G1 phase, instead of G2/M phase by LMB or Gefitinib24+LMB, indicating different mechanisms of LMB and KPT-185 in inducing the apoptosis of NSCLC cells.

In order to explore the synergism between gefitinib and LMB in A549, the inventors examined the expressions of a series of proteins, including EGFR, p-EGFR, Erk1/2, p-Erk1/2, Akt, and p-Akt, involving in EGFR pathways by comparing the differences between gefitinib treatments alone and gefitinib+LMB co-treatments. A previous study (Pathria et al., 2012) showed that CRM1 inhibition by LMB mediated apoptosis by hyperphosphorylation of Erk1/2 and induction of p21, but downregulated antiapoptotic survivin in melanoma cell lines. That may explain the observations in this study that the expressions of p-Erk1/2 and p-Akt were higher while survivin was lower in gefitinib+LMB co-treated A549 compared with gefitinib-treated A549. Therefore, the synergistic cytotoxic effects of LMB and gefitinib could result from their interactions on regulating Ras-Raf-MEK-Erk and PI3K-Akt pathways, two major downstream signaling routes of EGFR.

Gefitinib induced apoptosis of NSCLC cells through direct inhibition of pro-survival p-EGFR, p-Akt, and p-Erk1/2 (Mukohara et al., 2005; Zhao et al., 2016b), which was also manifested in this study by gefitinib treatment in A549. On the other hand, LMB, as a specific CRM1 inhibitor of the nuclear export signal (NES)-dependent transport (Lu et al., 2015), was found to significantly upregulate the expressions of p-Erk1/2 and p-Akt in A549 in the present study. The nuclear transport of Erk1/2 was reported to be inhibited by LMB and Erk1/2 entrapped in the nucleus could not be recycled back to the cytoplasm for the next round of activation (Adachi et al., 2000). Therefore, the anti-proliferative response induced by LMB could be explained by a loss of cytoplasmic/pro-survival Erk1/2 and hyperactivated nuclear p-Erk1/2 to induce apoptosis (Cagnol and Chambard, 2010; Pathria et al., 2012). The hyperactivated nuclear Akt based on this same mechanism as hyperactivated Erk1/2 by LMB treatment (Pathria et al., 2012), which is further demonstrated by the significantly higher p-Akt/total Akt ratios of gefitinib+LMB treatments than gefitinib treatments shown in this study. From this perspective, the synergistic effect of gefitinib and LMB could result from both deactivation of Erk1/2 and Akt in cytoplasm by gefitinib and entrapment of hyperactive p-Erk1/2 and p-Akt in the nucleus by LMB.

Gefitinib suppressed expressions of anti-apoptotic survivin in NSCLC cell lines through inhibition of the PI3K-Akt signaling pathway (Okamoto et al., 2010), which was also consistent with reduced expressions of p-Akt and survivin compared with control shown in this study. The lower expression of survivin in gefitinib+LMB treatment compared with gefitinib treatment in A549 should be attributed to the synergistic inhibition of cytoplasmic PI3K-Akt by gefitinib and LMB. Gefitinib treatment induced a decreased expression of the Cdk inhibitor p21 compared with control in A549 shown in this study, which may be associated with gefitinib-induced suppression of cytoplasmic Erk1/2 signaling (Meloche and Pouysségur, 2007). However, LMB treatment could induce significant upregulation of p21 compared with control in A549, which constitutes another important mechanism of synergism by gefitinib and LMB besides Ras-Raf-MEK-Erk and PI3K-Akt pathways. As a p53 downstream target gene, the elevated level of p21 in LMB-treated A549 resulted from activation/stabilization/nuclear accumulation of p53 by CRM1 inhibition (Shao et al., 2011; Lu et al., 2012) and resulted in the cell cycle arrest which was signified by increased G2/M and decreased G0/G1 fractions demonstrated as shown herein. In contrast, gefitinib mediated cell cycle arrest predominantly at the G0/G1 phase in A549, which is associated with overexpression of transducer of erbB2.1 (TOB1) and suppression of cyclin D1 (Sun et al., 2013). However, both p21 elevation and CRM1 inhibition could promote cyclin D1 nuclear accumulation (Alt et al., 2002) that may counteract the inhibitory effect of gefitinib on cyclin D1. That may also explain why fractions of G0/G1 phase in gefitinib+LMB co-treatments are significantly lower than gefitinib treatments, and the cell cycle arrest pattern is dominated by LMB (G2/M arrest) instead of gefitinib (G0/G1 arrest). Taken together, persistent nuclear Erk and Akt activities concomitant with loss of pro-survival/cytoplasmic Erk1/2 and Akt followed by a suppression of anti-apoptotic survivin as well as altered expressions of cell cycle regulator p21 revealed that the synergism of gefitinb and LMB in A549 is mediated through simultaneous involvements of multiple pathways impacted by CRM1 inhibition.

In some previous studies (Shen et al., 2012; Chen et al., 2013; Li et al., 2015b), the combinative therapeutics, such as aromatase or MEK inhibitors, enhanced the cytotoxicity of gefitinib in A549 by downregulating p-Akt and p-Erk1/2. On the other hand, combinative therapeutics, such as vATPase inhibitor or celecoxib (Jin et al., 2015; Li et al., 2015a), enhanced the cytotoxic sensitivity of A549 to gefitinib by modulating signaling pathways other than EGFR such as HIF-1α and cyclooxygenase-2. Therefore, the synergistic mechanism of LMB and gefitinib observed in the present study is a novel finding in comparison with the previously reported combinative therapeutics with gefitinib in A549, featured by enhanced p-Akt, p-Erk1/2, and p21 resulting from CRM1 inhibition.

No reported genetic modifications contributing to gefitinib-acquired resistance were observed in A549GR or A549GLR, including T790M point mutation and amplifications of genomic areas such as MET and HER2 (Sierra et al., 2010; Cortot and Jänne, 2014). On the other hand, activation of alternative pathways such as survivin and p-STAT3 as well as phenotypic transformations including significant changes in morphologies and EMT biomarkers were observed in A549GR. These alterations were frequently reported to be common mechanisms of acquired resistance of gefitinib (Sierra et al., 2010; Cortot and Jänne, 2014). The distinctive expression patterns of EGFR related signals also signify that the survival signaling pathways adopted by A549, A549GR, and A549GLR are significantly different, which lead to their different gefitinib sensitivities and tumorigenic properties. There were increased expressions of EGFR and p-EGFR in A549GR and A549GLR compared with A549. The increased mRNA expressions of EGFR in A549GR and A549GLR were also detected by qRT-PCR. On the other hand, the expression of p-Akt was significantly lower in A549GLR than A549 and A549GR while p-Erk1/2 was much lower in A549GR than A549 and A549GLR. Previous studies showed that downregulation of p-Akt by gefitinib treatment was not as significant as p-EGFR and p-Erk1/2 in gefitinib-resistant NSCLC cell lines (Koizumi et al., 2005; Kwak et al., 2005; Rho et al., 2009; Yamamoto et al., 2010). Although the chemical inhibition of p-Akt did not enhance the cytotoxic effect of gefitinib in gefitinib-resistant A549 (Rho et al., 2009), the function of downregulating p-Akt in reducing gefitinib-resistance remained unclear (Rho et al., 2009). This study showed that the significantly decreased expressions of p-Akt in A549GLR compared to A549GR may contribute to the much higher gefitinib sensitivities in A549GLR than A549GR. A previous study (Okamoto et al., 2012) also demonstrated that persistent activation of Akt-survivin signaling pathway conferred EGFR TKI erlotinib's resistance in NSCLC cell lines, and downregulation of survivin by short interfering RNA or survivin suppressor reversed the erlotinib-resistance. In line with these findings, the Western blot analyses further validated the simultaneous downregulation of p-Akt and survivin in A549GLR compared with A549GR is closely associated with the significant lower gefitinib resistance in A549GLR than A549GR. In addition, the expression of p-STAT3 in A549GLR was much lower in A549GLR than A549GR, which is consistent with the observations of the previous study showing that suppression of STAT3 activity could sensitize gefitinib-resistant NSCLC (Chiu et al., 2011).

In this study, A549GR showed typical EMT compared to A549, which is demonstrated by changes in morphology characterized by spindle-like shape and loss of cell-cell junctions as well as EMT biomarker expression changes characterized by repression of E-cadherin and gain of vimentin. EMT could contribute to enhanced cancer invasion and metastasis (Ghosh et al., 2012). This helps explain why A549GR showed a much stronger motility and invasive capacity in wound healing assay and transwell invasive assay. Azmi et al. recently demonstrated that 24-72 hrs treatments of CRM1 inhibitors including KPT-330, KPT-185, and LMB could reverse EMT in HEMCs and consequently induce growth inhibition and apoptosis, and prevent spheroid formation (Azmi et al., 2015). In this study, A549GLR treated by LMB for 10 months went through a non-traditional EMT as evidenced by a significant morphological change characterized by asterisk shape, increased expression of mesenchymal cell marker vimentin, as well as higher motility and invasive capacity compared with A549. However, a significant increased expression of epithelial cell marker E-cadherin and decreased mRNA expression of mesenchymal cell marker N-cadherin were also observed in A549GLR compared with A549 and A549GR, which may signify the capacity of the LMB co-treatment to suppress the gefitinib-induced EMT and resistance. Western blot and qRT-PCR analyses of this study further revealed that Twist1 and Snail1, negative regulators of E-cadherin (Peinado et al., 2007; Yang and Weinberg, 2008), were significantly downregulated in A549GLR compared with A549GR. EMT development, but not other resistant mechanisms including T790 mutation in EGFR exon 20 or amplifications of MET and HER2, has been shown to be correlated with gefitinib resistance in A549 (Rho et al., 2009). Similarly, in this study, both A549GR and A549GLR showed no T790 mutation or amplifications of MET and HER2, indicating that EMT may play a pivotal role in the development of gefitinib resistance in either A549GR or A549GLR.

EMT induction may also lead to emergence and/or enrichment of CSCs (Mani et al., 2008; Ghosh et al., 2012) which exhibited enhanced colony formation ability in soft agar due to their higher self-renewal capacity and stronger tumorigenic potential compared to non-resistant cancer cells. This is consistent with these observation that the colony number and size of A549GR are significantly higher than A549. The larger colony size but lower colony number of A549GLR than A549GR may also imply that A549GLR compromised a smaller fraction of CSCs which were selected by more cytotoxic gefitinib+LMB co-treatments compared with A549GR. Previous studies showed that EMT generated CSCs with increased expressions of CD44 and CD133 but decreased expression of CD24 in human mammary epithelial cells (HMLEs) and erlotinib-resistant H1650 NSCLC cell line (Mani et al., 2008; Ghosh et al., 2012). This is consistent with the expression pattern of CSC markers in A549GR. However, the decreased expression of CD44 in A549GLR compared with A549GR may further demonstrate the EMT suppressive function of gefitinib+LMB co-treatments (Cho et al., 2012).

The results of these studies demonstrated that LMB could not only overcome primary resistance but also delay acquired resistance of gefitinib in A549 at a concentration of 0.5 nM. Besides the interactions of pathways as mentioned above, the synergistic effect of LMB and gefitinib could depend on the concentration of LMB. The dose of 0.5 nM LMB selected for this study showed the maximized synergistic effects for different LMB doses tested (data not shown) and had a very low cytotoxic effect on A549 (89±4% of control) or H460 (92±5% of control). In fact, 0.5 nM LMB has been used in combination with doxorubicin or cisplatin in the inventors' previous studies (Lu et al., 2012; Gao et al., 2015). No acquired resistance of 0.5 nM LMB was observed in A549GLR (88±5% of control), while A549GR (96±3% of control) was more resistant to 0.5 nM LMB than A549GLR and A549 ($p<0.05$). In addition, the cross-resistances of A549GR and A549GLR against afatinib showed that IC50 of afatinib in A549GLR (8.0±1.5 μM) was much lower than A549GR (20.0±2.7 μM), showing that lung cancer cells co-treated by gefitinib+LMB would continue to benefit from the subsequent therapy using irreversible EGFR TKIs such as afatinib.

Besides A549, gefitinib+LMB also showed the synergistic effects on H460. Although both H460 and A549 have KRAS mutations, the differences in morphologies as well as inter and intra cellular heterogeneities between A549 and H460 are significant because A549 is a lung adenocarcinoma cell line while H460 is a large cell lung cancer cell line, and they are derived from different patients. Since EGFR TKIs such as gefitinib or afatinib is much more effective in treatments of NSCLC with mutant EGFR than wide type EGFR (such as A549 and H460), additional studies studying the combination of LMB with different EGFR TKIs in the treatments of EGFR-mutant NSCLC cell lines in vitro and in vivo can be conducted in accordance to the teachings of the present invention. Moreover, the investigations for clinical significance of LMB with the involvement of other clinically relevant molecular signatures in lung cancer or with other targeted therapeutics are warranted. Besides lung cancer, LMB was reported to have the potential to be applied in ovarian, pancreatic, and cervical cancers in which CRM1 is overexpressed and contributes to tumor progression and drug resistance (Lu et al., 2015). Gefitinib as single or combinative therapeutic agent has also been reported in clinical trials of breast cancer (Segovia-Mendoza et al., 2015), ovarian cancer (Posadas et al., 2007), pancreatic cancer (Brell et al., 2009), and cervical cancer (Goncalves et al., 2008). The mechanisms of action for gefitinib on these cancers include modulation of EGFR pathways such as PI3K/Akt, Raf1/Erk1/2, and cell cycle arrest (Zhou et al., 2009; Ohta et al., 2012; Segovia-Mendoza et al., 2015; Du et al., 2016). Therefore, gefitinib and LMB treatment may also be effective in treating these cancers with similar synergistic mechanisms, as reported herein.

In summary, the present study found that the combination therapy of LMB and gefitinib significantly increased the efficacy of gefitinib in A549 through regulation of EGFR pathway and cell cycle distribution. LMB co-treatment with gefitinib could effectively delay the development of the acquired resistance in A549 by reversing EMT and down-regulating Akt-survivin activation. These studies demonstrated that expressions of epithelial marker E-cadherin and mesenchymal marker vimentin could be two independent events in EMT. In vivo studies, different combinations of CRM1 inhibitors with EGFR TKIs, and clinical trials are necessary to fully validate the use of CRM1 inhibition as a novel therapeutic strategy to overcome the primary and acquired resistance of EGFR TKIs in NSCLC treatments, however the studies herein clearly demonstrate the synergistic activity of the present invention using well-known and validated model systems of cancer.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Adachi, M., Fukuda, M., Nishida, E., 2000. Nuclear Export of Map Kinase (ERK) Involves a Map Kinase Kinase (Mek-Dependent) Active Transport Mechanism. J. Cell Biol. 148, 849-856.

Alt, J. R., Gladden, A. B., Diehl, J. A., 2002. p21Cip1 promotes cyclin D1 nuclear accumulation via direct inhibition of nuclear export. J. Biol. Chem. 277, 8517-8523.

Azmi, A. S., Muqbil, I., Wu, J., Aboukameel, A., Senapedis, W., Baloglu, E., Bollig-Fischer, A., Dyson, G., Kauffman, M., Landesman, Y., 2015. Targeting the nuclear export protein XPO1/CRM1 reverses epithelial to mesenchymal transition. Sci. Rep. 5, 16077.

Brell, J. M., Matin, K., Evans, T., Volkin, R. L., Kiefer, G. J., Schlesselman, J. J., Dranko, S., Rath, L., Schmotzer, A., Lenzner, D., 2009. Phase II study of docetaxel and gefitinib as second-line therapy in gemcitabine pretreated patients with advanced pancreatic cancer. Oncology 76, 270-274.

Cagnol, S., Chambard, J. C., 2010. ERK and cell death: Mechanisms of ERK☐induced cell death-apoptosis, autophagy and senescence. FEBS J. 277, 2-21.

Chao, T.-T., Wang, C.-Y., Chen, Y.-L., Lai, C.-C., Chang, F.-Y., Tsai, Y.-T., Chao, C.-H. H., Shiau, C.-W., Huang, Y.-C. T., Yu, C.-J., 2015. Afatinib induces apoptosis in NSCLC without EGFR mutation through Elk-1-mediated suppression of CIP2A. Oncotarget 6, 2164.

Chen, J., Bi, H., Hou, J., Zhang, X., Zhang, C., Yue, L., Wen, X., Liu, D., Shi, H., Yuan, J., 2013. Atorvastatin overcomes gefitinib resistance in KRAS mutant human non-small cell lung carcinoma cells. Cell Death Dis. 4, e814.

Chiu, H.-C., Chou, D.-L., Huang, C.-T., Lin, W.-H., Lien, T.-W., Yen, K.-J., Hsu, J. T.-A., 2011. Suppression of Stat3 activity sensitizes gefitinib-resistant non small cell lung cancer cells. Biochem. Pharmacol. 81, 1263-1270.

Cho, S. H., Park, Y. S., Kim, H. J., Kim, C. H., Lim, S. W., Huh, J. W., Lee, J. H., Kim, H. R., 2012. CD44 enhances the epithelial-mesenchymal transition in association with colon cancer invasion. Int. J. Oncol. 41, 211-218.

Conde, E., Angulo, B., Tang, M., Morente, M., Torres-Lanzas, J., Lopez-Encuentra, A., Lopez-Rios, F., Sanchez-Cespedes, M., 2006. Molecular context of the EGFR mutations: evidence for the activation of mTOR/S6K signaling. Clin. Cancer Res. 12, 710-717.

Cortot, A. B., Jänne, P. A., 2014. Molecular mechanisms of resistance in epidermal growth factor receptor-mutant lung adenocarcinomas. Eur. Respir. Rev. 23, 356-366

Cromie, M. M., Gao, W., 2015. Epigallocatechin-3-gallate enhances the therapeutic effects of leptomycin B on human lung cancer a549 cells. Oxid. Med. Cell Longev. 2015.

Dragnev, K., You, M., Wang, Y., Lubet, R., 2013. Lung cancer chemoprevention: difficulties, promise and potential agents? Expert Opin. Investig. Drugs. 22, 35-47.

Du, J., Wang, L., Li, C., Yang, H., Li, Y., Hu, H., Li, H., Zhang, Z., 2016. MicroRNA-221 targets PTEN to reduce the sensitivity of cervical cancer cells to gefitinib through the PI3K/Akt signaling pathway. Tumor Biol. 37, 3939-3947.

Engelman, J. A., Zejnullahu, K., Mitsudomi, T., Song, Y., Hyland, C., Park, J. O., Lindeman, N., Gale, C.-M., Zhao, X., Christensen, J., 2007. MET amplification leads to gefitinib resistance in lung cancer by activating ERBB3 signaling. Science 316, 1039-1043.

Gao, W., Lu, C., Chen, L., Keohavong, P., 2015. Overexpression of CRM1: a characteristic feature in a transformed phenotype of lung carcinogenesis and a molecular target for lung cancer adjuvant therapy. J. Thorac. Oncol. 10, 815-825.

Ghosh, G., Lian, X., Kron, S. J., Palecek, S. P., 2012. Properties of resistant cells generated from lung cancer cell lines treated with EGFR inhibitors. BMC cancer 12, 95.

Goncalves, A., Fabbro, M., Lhomme, C., Gladieff, L., Extra, J.-M., Floquet, A., Chaigneau, L., Carrasco, A. T., Viens, P., 2008. A phase II trial to evaluate gefitinib as second- or third-line treatment in patients with recurring locoregionally advanced or metastatic cervical cancer. Gynecol Oncol. 108, 42-46.

Gridelli, C., De Marinis, F., Di Maio, M., Cortinovis, D., Cappuzzo, F., Mok, T., 2011. Gefitinib as first-line treatment for patients with advanced non-small-cell lung cancer with activating epidermal growth factor receptor mutation: Review of the evidence. Lung Cancer 71, 249-257.

Home, M., 2016. Should EGFR Tyrosine Kinase Inhibitors Be Used in Non-Small Cell Lung Cancer in the Absence of EGFR Mutations? Clinical Advances in Hematology & Oncology 14, 41-45

Huang, M.-H., Lee, J.-H., Chang, Y.-J., Tsai, H.-H., Lin, Y.-L., Lin, A. M.-Y., Yang, J. C.-H., 2013. MEK inhibitors reverse resistance in epidermal growth factor receptor mutation lung cancer cells with acquired resistance to gefitinib. Mol. Oncol. 7, 112-120.

Huang, Y.-C. T., 2014. Outdoor air pollution: a global perspective. J. Occup. Environ. Med. 56, S3-S7.

Jin, H. O., Hong, S. E., Kim, C. S., Park, J. A., Kim, J. H., Kim, J. Y., Kim, B., Chang, Y. H., Hong, S. I., Hong, Y. J., Park, I. C., Lee, J. K., 2015. Combined effects of EGFR tyrosine kinase inhibitors and vATPase inhibitors in NSCLC cells. Toxicol Appl Pharmacol. 287, 17-25.

Kancha, R. K., von Bubnoff, N., Miething, C., Peschel, C., Götze, K. S., Duyster, J., 2008. Imatinib and leptomycin B are effective in overcoming imatinib-resistance due to Bcr-Abl amplification and clonal evolution but not due to Bcr-Abl kinase domain mutation. Haematologica 93, 1718-1722.

Kazandjian, D., Blumenthal, G. M., Yuan, W., He, K., Keegan, P., Pazdur, R., 2016. FDA Approval of Gefitinib for the Treatment of Patients with Metastatic EGFR Mutation-Positive Non-Small Cell Lung Cancer. Clin. Cancer Res. 22, 1307-1312.

Kim, J., McMillan, E., Kim, H. S., Venkateswaran, N., Makkar, G., Rodriguez-Canales, J., Villalobos, P., Neggers, J. E., Mendiratta, S., Wei, S., 2016. XPO1-dependent nuclear export is a druggable vulnerability in KRAS-mutant lung cancer. Nature 538, 114-117.

Koehler, J., Schuler, M., 2013. Afatinib, erlotinib and gefitinib in the first-line therapy of EGFR mutation-positive lung adenocarcinoma: a review. Onkologie. 36, 510-518.

Koizumi, F., Shimoyama, T., Taguchi, F., Saijo, N., Nishio, K., 2005. Establishment of a human non small cell lung cancer cell line resistant to gefitinib. Int. J. Cancer. 116, 36-44.

Kwak, E. L., Sordella, R., Bell, D. W., Godin-Heymann, N., Okimoto, R. A., Brannigan, B. W., Harris, P. L., Driscoll, D. R., Fidias, P., Lynch, T. J., 2005. Irreversible inhibitors of the EGF receptor may circumvent acquired resistance to gefitinib. Proc. Natl. Acad. Sci. USA. 102, 7665-7670.

Lee, C. K., Brown, C., Gralla, R. J., Hirsh, V., Thongprasert, S., Tsai, C.-M., Tan, E. H., Ho, J. C.-M., Zaatar, A., Sanchez, J. A. O., 2013. Impact of EGFR inhibitor in non-small cell lung cancer on progression-free and overall survival: a meta-analysis. J. Natl. Cancer Inst. 105,595-605.

Li, N., Li, H., Su, F., Li, J., Ma, X., Gong, P., 2015a. Relationship between epidermal growth factor receptor (EGFR) mutation and serum cyclooxygenase-2 Level, and the synergistic effect of celecoxib and gefitinib on EGFR expression in non-small cell lung cancer cells. Int. J. Clin. Exp. Pathol. 8, 9010.

Li, S., Chen, S., Jiang, Y., Liu, J., Yang, X., Quan, S., 2015b. Synergistic interaction between MEK inhibitor and gefitinib in EGFR TKI resistant human lung cancer cells. Oncol. Lett. 10, 2652-2656.

Lo, H. W., Ali Seyed, M., Wu, Y., Bartholomeusz, G., Hsu, S. C., Hung, M. C., 2006. Nuclear cytoplasmic transport of EGFR involves receptor endocytosis, importin $\beta 1$ and CRM1. J. Cell Biochem. 98, 1570-1583.

Lu, C., A Figueroa, J., Liu, Z., Konala, V., Aulakh, A., Verma, R., Cobos, E., Chiriva-Internati, M., Gao, W., 2015. Nuclear Export as a Novel Therapeutic Target: The CRM1 Connection. Curr. Cancer Drug Targets 15, 575-592.

Lu, C., Shao, C., Cobos, E., Singh, K. P., Gao, W., 2012. Chemotherapeutic sensitization of leptomycin B resistant lung cancer cells by pretreatment with doxorubicin. PLoS One 7, e32895.

Lv, T., Wang, Q., Cromie, M., Liu, H., Tang, S., Song, Y., Gao, W., 2015. Twist1-mediated 4E-BP1 regulation through mTOR in non-small cell lung cancer. Oncotarget 6, 33006-33018.

Mani, S. A., Guo, W., Liao, M.-J., Eaton, E. N., Ayyanan, A., Zhou, A. Y., Brooks, M., Reinhard, F., Zhang, C. C., Shipitsin, M., 2008. The epithelial-mesenchymal transition generates cells with properties of stem cells. Cell 133, 704-715.

Marquez-Medina, D., Popat, S., 2016. Eventual role of EGFR-tyrosine kinase inhibitors in early-stage non-small-cell lung cancer. Future Oncol. 12, 815-825.

Meloche, S., Pouysségur, J., 2007. The ERK1/2 mitogen-activated protein kinase pathway as a master regulator of the G1-to S-phase transition. Oncogene 26, 3227-3239.

Mukohara, T., Engelman, J. A., Hanna, N. H., Yeap, B. Y., Kobayashi, S., Lindeman, N., Halmos, B., Pearlberg, J., Tsuchihashi, Z., Cantley, L. C., 2005. Differential effects of gefitinib and cetuximab on non-small-cell lung cancers bearing epidermal growth factor receptor mutations. J. Natl. Cancer Inst. 97, 1185-1194.

Mutka, S. C., Yang, W. Q., Dong, S. D., Ward, S. L., Craig, D. A., Timmermans, P. B., Murli, S., 2009. Identification of nuclear export inhibitors with potent anticancer activity in vivo. Cancer Res. 69, 510-517.

Nakaya, Y., Sheng, G., 2013. EMT in developmental morphogenesis. Cancer Lett. 341, 9-15.

Newlands, E., Rustin, G., Brampton, M., 1996. Phase I trial of elactocin. Br. J. Cancer. 74, 648-649.

Nguyen, K.-S. H., Kobayashi, S., Costa, D. B., 2009. Acquired resistance to epidermal growth factor receptor tyrosine kinase inhibitors in non-small-cell lung cancers dependent on the epidermal growth factor receptor pathway. Clin. lung Cancer 10, 281-289.

Ohta, T., Ohmichi, M., Shibuya, T., Takahashi, T., Tsutsumi, S., Takahashi, K., Kurachi, H., 2012. Gefitinib (ZD1839) increases the efficacy of cisplatin in ovarian cancer cells. Cancer Biol. Ther. 13, 408-416.

Okamoto, K., Okamoto, I., Hatashita, E., Kuwata, K., Yamaguchi, H., Kita, A., Yamanaka, K., Ono, M., Nakagawa, K., 2012. Overcoming erlotinib resistance in EGFR mutation-positive non-small cell lung cancer cells by targeting survivin. Mol. Cancer Ther. 11, 204-213.

Okamoto, K., Okamoto, I., Okamoto, W., Tanaka, K., Takezawa, K., Kuwata, K., Yamaguchi, H., Nishio, K., Nakagawa, K., 2010. Role of survivin in EGFR inhibitor-induced apoptosis in non-small cell lung cancers positive for EGFR mutations. Cancer Res. 70, 10402-10410.

Pao, W., Miller, V. A., Politi, K. A., Riely, G. J., Somwar, R., Zakowski, M. F., Kris, M. G., Varmus, H., 2005a. Acquired resistance of lung adenocarcinomas to gefitinib or erlotinib is associated with a second mutation in the EGFR kinase domain. PLoS Med. 2, e73.

Pao, W., Wang, T. Y., Riely, G. J., Miller, V. A., Pan, Q., Ladanyi, M., Zakowski, M. F., Heelan, R. T., Kris, M. G., Varmus, H. E., 2005b. KRAS mutations and primary resistance of lung adenocarcinomas to gefitinib or erlotinib. PLoS Med. 2, e17.

Pathria, G., Wagner, C., Wagner, S. N., 2012. Inhibition of CRM1-mediated nucleocytoplasmic transport: triggering human melanoma cell apoptosis by perturbing multiple cellular pathways. J. Invest. Dermatol. 132, 2780-2790.

Peinado, H., Olmeda, D., Cano, A., 2007. Snail, Zeb and bHLH factors in tumour progression: an alliance against the epithelial phenotype? Nat. Rev. Cancer. 7, 415-428.

Posadas, E. M., Liel, M. S., Kwitkowski, V., Minasian, L., Godwin, A. K., Hussain, M. M., Espina, V., Wood, B. J., Steinberg, S. M., Kohn, E. C., 2007. A phase II and pharmacodynamic study of gefitinib in patients with refractory or recurrent epithelial ovarian cancer. Cancer 109, 1323-1330.

Rho, J. K., Choi, Y. J., Lee, J. K., Ryoo, B.-Y., Yang, S. H., Kim, C. H., Lee, J. C., 2009. Epithelial to mesenchymal transition derived from repeated exposure to gefitinib determines the sensitivity to EGFR inhibitors in A549, a non-small cell lung cancer cell line. Lung Cancer 63, 219-226.

Segovia-Mendoza, M., González-González, M. E., Barrera, D., Diaz, L., García-Becerra, R., 2015. Efficacy and mechanism of action of the tyrosine kinase inhibitors gefitinib, lapatinib and neratinib in the treatment of HER2-positive breast cancer: preclinical and clinical evidence. Am. J. Cancer Res. 5, 2531-2561.

Shao, C., Lu, C., Chen, L., Koty, P. P., Cobos, E., Gao, W., 2011. p53-Dependent anticancer effects of leptomycin B on lung adenocarcinoma. Cancer Chemother. Pharmacol. 67, 1369-1380.

Shen, L., Li, Z., Shen, S., Niu, X., Yu, Y., Li, Z., Liao, M., Chen, Z., Lu, S., 2012. The synergistic effect of EGFR tyrosine kinase inhibitor gefitinib in combination with aromatase inhibitor anastrozole in non-small cell lung cancer cell lines. Lung Cancer 78, 193-200.

Sierra, J. R., Cepero, V., Giordano, S., 2010. Molecular mechanisms of acquired resistance to tyrosine kinase targeted therapy. Mol. Cancer. 9, 75.

Sos, M. L., Rode, H. B., Heynck, S., Peifer, M., Fischer, F., Klüter, S., Pawar, V. G., Reuter, C., Heuckmann, J. M., Weiss, J., 2010. Chemogenomic profiling provides insights into the limited activity of irreversible EGFR Inhibitors in tumor cells expressing the T790M EGFR resistance mutation. Cancer Res. 70, 868-874.

Sun, K. K., Yang, Y., Zhao, L., Wang, L. L., Jiao, Y., 2013. Transducer of erbB2. 1 is a potential cellular target of gefitinib in lung cancer therapy. Oncol. Lett. 5, 373-377.

Tartarone, A., Lazzari, C., Lerose, R., Conteduca, V., Improta, G., Zupa, A., Bulotta, A., Aieta, M., Gregorc, V., 2013. Mechanisms of resistance to EGFR tyrosine kinase inhibitors gefitinib/erlotinib and to ALK inhibitor crizotinib. Lung Cancer 81, 328-336.

Turner, J. G., Dawson, J., Cubitt, C. L., Baz, R., Sullivan, D. M., 2014. Inhibition of CRM1-dependent nuclear export sensitizes malignant cells to cytotoxic and targeted agents, Seminars in cancer biology. Semin. Cancer Biol. 27, 62-73.

Wang, S., Han, X., Wang, J., Yao, J., Shi, Y., 2014. Antitumor effects of a novel chromosome region maintenance 1 (CRM1) inhibitor on non-small cell lung cancer cells in vitro and in mouse tumor xenografts. PLoS One 9, e89848.

Wang, Y., Zhang, Z., Wang, H., Zhang, Y., Ji, M., Xu, H., Wang, C., Sun, Z., Gao, W., Wang, S.-L., 2016. miR-138-1* regulates aflatoxin B1-induced malignant transformation of BEAS-2B cells by targeting PDK1. Arch. Toxicol. 90, 1239-1249.

Yamamoto, C., Basaki, Y., Kawahara, A., Nakashima, K., Kage, M., Izumi, H., Kohno, K., Uramoto, H., Yasumoto, K., Kuwano, M., 2010. Loss of PTEN expression by blocking nuclear translocation of EGR1 in gefitinib-resistant lung cancer cells harboring epidermal growth factor receptor-activating mutations. Cancer Res. 70, 8715-8725

Yang, J., Weinberg, R. A., 2008. Epithelial-mesenchymal transition: at the crossroads of development and tumor metastasis. Dev. Cell 14, 818-829.

Zhao, R., Zhou, S., Xia, B., Zhang, C.-y., Hai, P., Zhe, H., Wang, Y.-y., 2016a. AT-101 enhances gefitinib sensitivity in non-small cell lung cancer with EGFR T790M mutations. BMC cancer 16, 491.

Zhao, Z. Q., Yu, Z. Y., Li, J., Ouyang, X. N., 2016b. Gefitinib induces lung cancer cell autophagy and apoptosis via blockade of the PI3K/AKT/mTOR pathway. Oncol. Lett. 12, 63-68.

Zhou, X., Zheng, M., Chen, F., Zhu, Y., Yong, W., Lin, H., Sun, Y., Han, X., 2009. Gefitinib inhibits the proliferation of pancreatic cancer cells via cell cycle arrest. Anat. Rec. 292, 1122-1127.

Zhu, Y., He, W., Gao, X., Li, B., Mei, C., Xu, R., Chen, H., 2015. Resveratrol overcomes gefitinib resistance by increasing the intracellular gefitinib concentration and triggering apoptosis, autophagy and senescence in PC9/G NSCLC cells. Sci Rep. 5, 17730.

---

What is claimed is:

1. A composition for treatment of a KRAS expressing lung cancer that has become refractory to an EGFR inhibitor comprising in a single dose an amount of a CRM1 inhibitor to achieve a concentration of 0.5 nM and an EGRF inhibitor to achieve a concentration of 12 to 64 µM administered concurrently that is synergistic for the treatment of the KRAS expressing lung cancer that has become refractory to the EGFR inhibitor when compared to an additive effect of the CRM1 inhibitor and the EGRF inhibitor when used alone; wherein the CRM1 inhibitor is Leptomycin B, and the EGFR inhibitor is selected from gefitinib or afatinib.

2. The composition of claim 1, wherein the lung cancer is selected from non-small cell lung cancer, a lung adenocarcinoma, or a bronchioloalveolar carcinoma.

3. The composition of claim 1, wherein the composition is adapted for oral, intranasal, pulmonary, intraperitoneal, intravenous, vaginal, rectal, intramuscular, aerosol, nasal spray, transdermal, or colonic administration.

4. The composition of claim 1, further comprising one or more pharmaceutically acceptable carriers.

5. The composition of claim 1, wherein the composition is adapted for sustained release.

* * * * *

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gatcgcattc atgcgtcttc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tccccatggc aaactcttgc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
cgcattcatg cgtcttcacc                                              20

<210> SEQ ID NO 4
<211> LENGTH: 22
<212> TYPE: DNA
<213> ORGANISM: Artificial Sequence
```

```
<220> FEATURE:
<223> OTHER INFORMATION: Synthetic primer

<400> SEQUENCE: 4
ccatccagtg tctccagaag tg                                          22

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
ttcccagtga taaccagtgt gtag                                        24

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
ccatcttcct gctgctgtaa ctg                                         23

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gccttctctg ccaactgtcc                                             20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
acaaccaagt gaggcaggtc                                             20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
gtattgttca gcgggtctcc                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ggtcttgcca gacaccaaag                                             20
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tgagaggaca cacgcaaaac                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
ctgcgtctct tgccggaatg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ttggctcacc ctccagaagg                                               20

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

<400> SEQUENCE: 14
ttgccagttg tggtgatc                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15
agacccagaa ggagaagc                                                 18

<210> SEQ ID NO 16
<211> LENGTH: 15
<212> TYPE: DNA
<213> ORGANISM: Artificial Sequence
<220> FEATURE:
<223> OTHER INFORMATION: Synthetic primer

<400> SEQUENCE: 16
tgccccgacg ttgcc                                                    15

<210> SEQ ID NO 17
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 17
cagttcttga atgtagagat gcggt                                          25

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
cgggaatgca gttgaggatc                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
aggatggtgt aagcgatggc                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
cctttcactg cggtacagtg                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
gatccagggg ctttgtcacc                                                20

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
cttgaacgga aagtggaatc ct                                             22

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
gtcaggcttg gaaacgtcc                                                 19

<210> SEQ ID NO 24
```

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 24
ggctcagcta cgccttctc                                                    19

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
tccttctctg gaaacaatga ca                                                22

<210> SEQ ID NO 26
<211> LENGTH: 19
<212> TYPE: DNA
<213> ORGANISM: Artificial Sequence
<220> FEATURE:
<223> OTHER INFORMATION: Synthetic primer

<400> SEQUENCE: 26
cgcgctcttt cctcgtcag                                                    19

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tcccagatga gcattggcag                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tgctcctacc cacgcagatt                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
agaccacgaa gagactggct                                                   20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
```

```
cccagatgga gaaagctctg                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
gttgtttgct gcacagatgg                                                    20

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
gggatggtgc cttgagtga                                                     19

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
gttcctgggc agaagaggag                                                    20
```